(12) United States Patent
Duncan

(10) Patent No.: US 11,529,145 B2
(45) Date of Patent: Dec. 20, 2022

(54) OCCLUSION DEVICES AND METHODS OF THEIR MANUFACTURE AND USE

(71) Applicant: W. L. Gore & Associates, Inc., Newark, DE (US)

(72) Inventor: Jeffrey B. Duncan, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 616 days.

(21) Appl. No.: 16/454,640

(22) Filed: Jun. 27, 2019

(65) Prior Publication Data

US 2019/0314030 A1 Oct. 17, 2019

Related U.S. Application Data

(62) Division of application No. 13/738,733, filed on Jan. 10, 2013, now Pat. No. 10,342,548.

(Continued)

(51) Int. Cl.
*A61B 17/12* (2006.01)
*A61B 17/00* (2006.01)
*A61B 90/00* (2016.01)

(52) U.S. Cl.
CPC ...... *A61B 17/1214* (2013.01); *A61B 17/1204* (2013.01); *A61B 17/1215* (2013.01);
(Continued)

(58) Field of Classification Search
CPC .......... A61B 17/1214; A61B 17/12031; A61B 17/12036; A61B 17/1204; A61B 17/12109; A61B 17/12113; A61B 17/12145; A61B 17/1215; A61B 2017/00858; A61B 2090/3966; A61B 2017/00526; A61B 2017/00778; A61B 2017/00867; A61B 2017/00871; A61B 2017/00884; A61B 2017/00995
See application file for complete search history.

(56) References Cited

U.S. PATENT DOCUMENTS 4,706,671 A  11/1987  Weinrib
5,192,286 A  3/1993  Phan et al.
(Continued)

FOREIGN PATENT DOCUMENTS

AU   35101/01 A   6/2001
CA   2186768 C    12/2000
(Continued)

OTHER PUBLICATIONS

European Search Report from EP17202458.0, dated Mar. 26, 2018, 8 pages.

(Continued)

*Primary Examiner* — George J Ulsh
*Assistant Examiner* — Rachel S Highland

(57) ABSTRACT

Disclosed are implantable medical devices for the occlusion of a bodily lumen, cavity, vessel, or organ, as well as methods for manufacturing such occlusion devices, and methods for treating a subject using the occlusion devices. The devices generally include a wire having shape memory properties and a flexible membranous material disposed about the wire. Some embodiments include a lateral fringe on the membranous material. Some embodiments include a fluid capture cup affixed to the wire.

20 Claims, 12 Drawing Sheets

Related U.S. Application Data

(60) Provisional application No. 61/586,633, filed on Jan. 13, 2012.

(52) U.S. Cl.
CPC .. *A61B 17/12031* (2013.01); *A61B 17/12036* (2013.01); *A61B 17/12109* (2013.01); *A61B 17/12113* (2013.01); *A61B 17/12145* (2013.01); *A61B 2017/00526* (2013.01); *A61B 2017/00778* (2013.01); *A61B 2017/00858* (2013.01); *A61B 2017/00867* (2013.01); *A61B 2017/00871* (2013.01); *A61B 2017/00884* (2013.01); *A61B 2017/00995* (2013.01); *A61B 2090/3966* (2016.02)

(56) References Cited

U.S. PATENT DOCUMENTS

| | | | |
|---|---|---|---|
| 5,334,210 | A | 8/1994 | Gianturco |
| 5,656,036 | A | 8/1997 | Palmaz |
| 5,766,219 | A | 6/1998 | Horton |
| 5,836,913 | A | 11/1998 | Orth et al. |
| 6,117,157 | A | 9/2000 | Tekulve |
| 6,391,037 | B1 | 5/2002 | Greenhalgh |
| 6,554,849 | B1 | 4/2003 | Jones et al. |
| 6,638,293 | B1 | 10/2003 | Makower et al. |
| 6,656,207 | B2 | 12/2003 | Epstein et al. |
| 6,702,834 | B1 | 3/2004 | Boylan et al. |
| 6,712,836 | B1 | 3/2004 | Berg et al. |
| 7,229,461 | B2 | 6/2007 | Chin et al. |
| 7,550,004 | B2 | 6/2009 | Bahler et al. |
| 7,883,516 | B2 | 2/2011 | Huang et al. |
| 7,896,899 | B2 | 3/2011 | Patterson et al. |
| 8,043,321 | B2 | 10/2011 | Elliott |
| 8,167,935 | B2 | 5/2012 | McGuckin et al. |
| 9,301,764 | B2 | 4/2016 | White et al. |
| 10,342,548 | B2 | 7/2019 | Duncan |
| 2001/0003801 | A1 | 6/2001 | Strecker |
| 2003/0171771 | A1 | 9/2003 | Anderson et al. |
| 2003/0176884 | A1 | 9/2003 | Berrada et al. |
| 2003/0229366 | A1 | 12/2003 | Reggie et al. |
| 2005/0272211 | A1* | 12/2005 | Browne .................. B60J 10/00 438/296 |
| 2006/0116709 | A1 | 6/2006 | Sepetka et al. |
| 2006/0206140 | A1 | 9/2006 | Shaolian et al. |
| 2006/0271086 | A1 | 11/2006 | Ramzipoor et al. |
| 2007/0027526 | A1 | 2/2007 | Demetriades et al. |
| 2007/0050007 | A1 | 3/2007 | Kondyurin et al. |
| 2007/0082021 | A1 | 4/2007 | Bates |
| 2008/0097401 | A1 | 4/2008 | Trapp et al. |
| 2008/0097508 | A1 | 4/2008 | Jones et al. |
| 2008/0221554 | A1 | 9/2008 | O'Connor et al. |
| 2008/0302368 | A1 | 12/2008 | McGuckin et al. |
| 2009/0018569 | A1 | 1/2009 | Desai et al. |
| 2009/0018636 | A1 | 1/2009 | Gailloud et al. |
| 2009/0138065 | A1* | 5/2009 | Zhang ...................... A61F 2/95 623/1.12 |
| 2009/0187098 | A1 | 7/2009 | Makower et al. |
| 2009/0297582 | A1 | 12/2009 | Meyer et al. |
| 2010/0016885 | A1* | 1/2010 | Eidenschink .......... A61B 1/018 606/213 |
| 2011/0295303 | A1* | 12/2011 | Freudenthal ..... A61B 17/12022 606/200 |
| 2012/0158034 | A1* | 6/2012 | Wilson ............. A61B 17/12181 606/192 |
| 2012/0226304 | A1 | 9/2012 | Ryan et al. |
| 2019/0314030 | A1 | 10/2019 | Duncan |

FOREIGN PATENT DOCUMENTS

| | | |
|---|---|---|
| EP | 1733702 A2 | 12/2006 |
| JP | 2001-509054 A | 7/2001 |
| JP | 2009-502343 A | 1/2009 |
| JP | 2009-504330 A | 2/2009 |
| WO | 94/07560 A1 | 4/1994 |
| WO | 97/27893 A1 | 8/1997 |
| WO | 01/64112 A1 | 9/2001 |
| WO | 2004/010878 A1 | 2/2004 |
| WO | 2005/042081 A1 | 5/2005 |
| WO | 2007/016166 A2 | 2/2007 |
| WO | 2008/106171 A1 | 9/2008 |
| WO | 2010/029190 A1 | 3/2010 |
| WO | 2010/115076 A2 | 10/2010 |
| WO | 2010/135352 A1 | 11/2010 |

OTHER PUBLICATIONS

International Preliminary Report on Patentability received for PCT Patent Application No. PCT/US13/21209, dated Jul. 24, 2014, 16 pages.
International Search Report for PCT/US2013/021209 dated Sep. 18, 2013, corresponding to U.S. Appl. No. 13/738,733.
International Written Opinion received for PCT Patent Application No. PCT/US13/21209, dated Sep. 18, 2013, 14 pages.

* cited by examiner

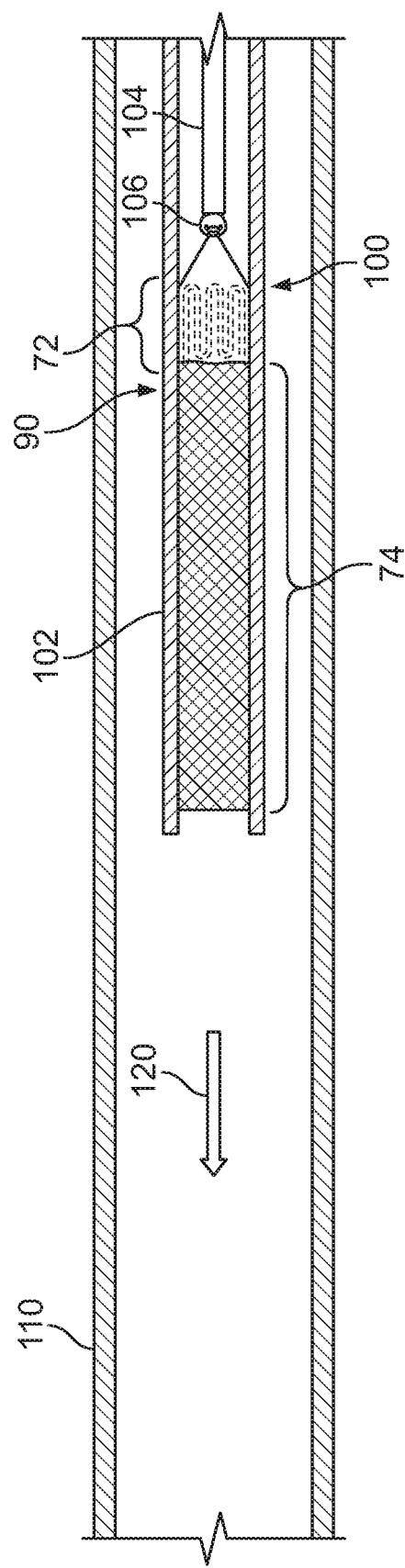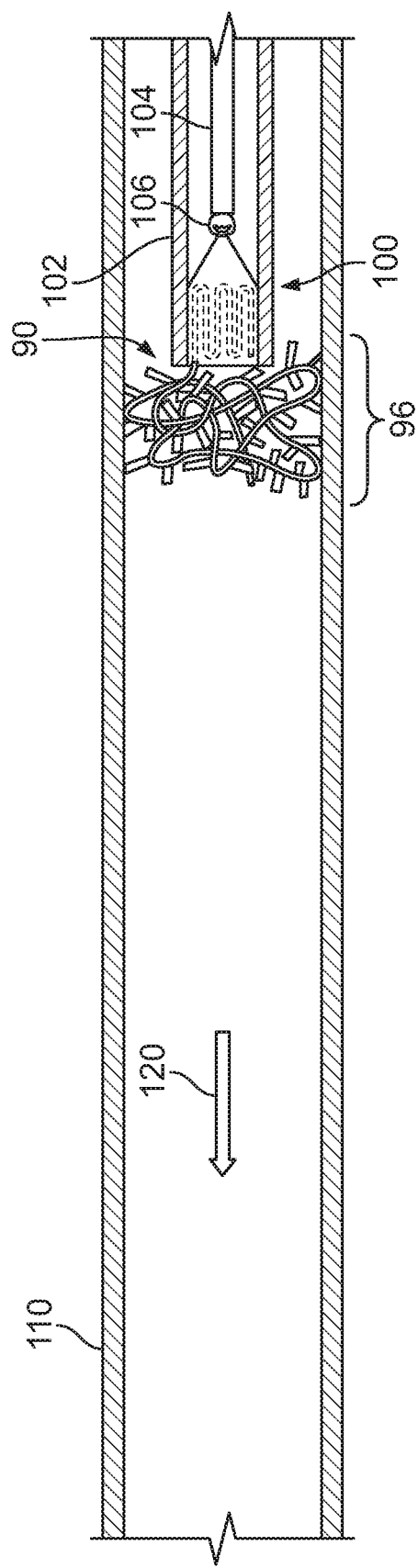
FIG. 10A
FIG. 10B

OCCLUSION DEVICES AND METHODS OF THEIR MANUFACTURE AND USE

CROSS-REFERENCE TO RELATED APPLICATIONS

This application is a divisional of U.S. application Ser. No. 13/738,733, filed on Jan. 10, 2013, which claims the benefit of priority of U.S. Provisional Application No. 61/586,633, filed Jan. 13, 2012. The disclosure of the prior applications are considered part of (and are incorporated by reference in) the disclosure of this application.

TECHNICAL FIELD

This disclosure relates generally to medical devices, and more specifically to devices for occlusion of a bodily lumen, cavity, vessel, or organ.

BACKGROUND

Many clinical situations require the reduction or complete stoppage of fluid flow (e.g., blood flow) in some region of a patient's body. Treatments for aneurysms, arteriovenous malformations, traumatic fistulae, and tumor embolization provide a few notable examples. These and other conditions often require that the fluid flow through at least a portion of a bodily lumen, cavity, vessel, or organ be blocked.

Occluders, plugs, and embolic coils are examples of devices that can be implanted in a patient to block fluid flow in a lumen, cavity, or organ. In some cases, the implanted device alone sufficiently provides the desired blockage. In some cases, the implanted device induces thrombosis, and the combination of the device and the thrombus provide the desired blockage. For example, vascular occlusion devices may be deployed within a blood vessel at the site of an aneurysm, or within the aneurysm, of the brain or limbs. During deployment, the configuration of the device may change to an operational size and shape to reduce the flow of blood through the weakened section of the blood vessel. Thrombus may form on the occlusion device to further seal off blood flow in the area of the aneurysm, thereby preventing its ballooning or rupture. A typical intracranial procedure would consist of placing one or more coils into the aneurysm to fill the void, thus causing thrombus to form, and reducing the pressure within the aneurysm. Often this is done through a stent or "stentriever" to help prevent protrusion of the coil into the lumen of the vessel.

An embolic coil is a type of vascular occlusion device. Embolic coils can be constructed from a biocompatible metal wire, such as a shape memory metal alloy. Use of a shape memory material may allow the device to be arranged in a low-profile configuration for transcatheter deployment, and for the device to expand to an operational size and shape when deployed at the target location within the patient's vasculature.

SUMMARY

This disclosure provides implantable medical devices for the occlusion of a bodily lumen, cavity, vessel, or organ. This disclosure also provides methods for manufacturing such occlusion devices, and methods for treating a subject using the occlusion devices.

Particular embodiments of the subject matter described in this specification can be implemented so as to realize one or more of the following advantages. In some embodiments, the implantable occlusion devices are functionally enhanced by the inclusion of membranous materials to increase the profile size and the thrombogenicity of the occlusion devices. In some embodiments, the membranous material on the occlusion devices is configured as multiple elongated fringe members to enhance the profile size and the thrombogenicity of the occlusion devices. In some embodiments, the occlusion devices are functionally enhanced by the inclusion of a membranous cup-shaped portion configured in an everted arrangement that substantially blocks fluid flow from passing through the occlusion device.

Disclosed are devices for full or partial occlusion of a lumen, cavity, vessel, or organ in a bodily tissue. The devices provided herein can be used to treat, for example, aneurysms, arteriovenous malformations, traumatic fistulae, endoleaks, wounds, various cancers, and many other conditions. The disclosed devices include, for example, occluders, coils, and plugs. In some embodiments, the occlusion devices provided herein include at least one wire and a membranous material. In some embodiments, the membranous material is disposed around the wire (e.g., by wrapping) and may be incised along at least a portion of its length to form a fringe extending outwardly from and exterior to the wire. The incisions effectively generate an external fringe having filaments or strips extending along the wire. In some embodiments, for example those including an elastomeric membranous material, the occlusion devices provided herein are not incised to form fringes. In some embodiments, the occlusion devices provided herein include a cup formed of the membranous material. In some embodiments, the cup is adapted to substantially block fluid flow through the device to aid in occluding or limiting fluid flow through the lumen.

In one general aspect, an implantable occlusion device comprises at least one wire having shape memory properties and a flexible polymer sheet; the sheet is disposed around the wire, and the sheet includes an external fringe along at least a portion of a length of the sheet.

In various implementations the external fringe may comprise an incised portion of the sheet; at least a portion of the fringe may be non-integral to the sheet; the fringe may extend substantially an entire length of the wire; the sheet may be attached to the wire at one or more locations on the wire; the sheet may comprise ePTFE; the implantable occlusion device may further comprise an endothelization promoting agent, anti-inflammatory agent, or a healing agent; and the implantable occlusion device may further comprise one or more radiopaque markers.

In a second general aspect, an implantable occlusion device comprises at least one wire having shape memory properties and a flexible polymer tube; the tube is disposed around the wire, and the tube includes an external fringe along at least a portion of a length of the tube.

In various implementations at least a portion of the wire may be located inside a lumen of the tube; the tube may comprise a polymer strip that is wrapped around at least a portion of the wire; the external fringe may comprise an incised portion of the tube; at least a portion of the fringe may be non-integral to the tube; the fringe may extend substantially an entire length of the wire; the fringe may have a length that extends beyond a length of the wire; the tube may be attached to the wire at one or more locations on the wire; the tube may comprise ePTFE; the implantable occlusion device may further comprise an endothelization promoting agent, anti-inflammatory agent, or a healing agent; and the implantable occlusion device may further comprise one or more radiopaque markers.

In a third general aspect, a method of making an implantable occlusion device comprises providing at least one shape memory wire and forming the shape memory wire into a coil, the coil having an overall outside diameter and a coil length; providing a flexible polymeric tube, the flexible polymeric tube having an inside diameter that is smaller than the overall outside diameter of the coil; elongating the coil, wherein the elongated coil has an elongated coil length that is greater than the coil length, and wherein the elongated coil has an elongated coil diameter that is less than the overall outside diameter of the coil; fitting the flexible polymeric tube over the elongated coil; and allowing the elongated coil to recoil to a contracted length, wherein the contracted length is less than the elongated coil length, thereby causing the flexible polymeric tube to form an irregular shape useful for occlusion.

In various implementations the coil may be a substantially helical coil; the flexible polymeric material may comprise ePTFE; the method of making an implantable occlusion device may further comprise attaching the flexible polymeric material to the elongated coil prior to allowing the elongated helical coil to recoil to the contracted length; the method of making an implantable occlusion device may further comprise attaching the flexible polymeric material to the elongated coil on an entire length of the wire; the method of making an implantable occlusion device may further comprise attaching the flexible polymeric material to the elongated coil at multiple discrete attachment points along a length of the elongated coil; the method of making an implantable occlusion device may further comprise attaching the flexible polymeric material to the elongated coil using an adhesive; and the method of making an implantable occlusion device may further comprise, prior to allowing the elongated coil to recoil to the contracted length, incising the flexible polymeric material to create a fringe portion along at least a portion of a length of the flexible polymeric material.

In a fourth general aspect, a device for limiting fluid flow through a lumen in a bodily tissue comprises at least one wire with proximal and distal ends; and a flexible polymeric cup, wherein the flexible polymeric cup includes an open end affixed to the proximal end of the wire, wherein the flexible polymeric cup is adapted to be reconfigured during deployment into the lumen from a pre-deployed state to an everted state, and wherein the flexible polymeric cup in the everted state is adapted to limit fluid flow through the lumen.

In various implementations the flexible polymeric cup may be formed from a sheet of polymeric material; the flexible polymeric cup may be formed from a tube of polymeric material; the flexible polymeric cup may comprise ePTFE; the device for limiting fluid flow through a lumen in a bodily tissue may further comprise one or more radiopaque markers; and the device for limiting fluid flow through a lumen in a bodily tissue may further comprise a flexible polymeric material, the flexible polymeric material may be disposed around the wire, and the flexible polymeric material may include an external fringe along at least a portion of a length of the flexible polymeric material.

In a fifth general aspect, a method for occluding a lumen in a bodily tissue comprises providing an occlusion device, wherein the occlusion device comprises: at least one wire with proximal and distal ends and a flexible polymeric cup, wherein the flexible polymeric cup includes an open end affixed to the proximal end of the wire, wherein the flexible polymeric cup is adapted to be reconfigured during deployment into the lumen from a pre-deployed state to an everted state, and wherein the flexible polymeric cup in the everted state is adapted to occlude the lumen; providing a delivery sheath, wherein the delivery sheath comprises a delivery lumen; configuring, within the delivery lumen, the occlusion device in the pre-deployed state; delivering the delivery lumen including the occlusion device in the pre-deployed state to a target site within the lumen; and deploying the occlusion device at the target site within the lumen, wherein the deploying comprises: ejecting the occlusion device from the delivery lumen and reconfiguring the flexible polymeric cup from the pre-deployed state to the everted state.

In various implementations the reconfiguring of the flexible polymeric cup from the pre-deployed state to the everted state may be caused at least partially by pressure exerted by fluid against the flexible polymeric cup; and the reconfiguring of the flexible polymeric cup from the pre-deployed state to the everted state may be caused at least partially by pressure exerted by a device against the flexible polymeric cup.

In a sixth general aspect, a method of making an implantable occlusion device comprises providing at least one shape memory wire; forming the shape memory wire into a cup frame, the cup frame having an overall outside diameter and open proximal and distal ends; and affixing a flexible polymeric cup to the proximal end of the cup frame, wherein the flexible polymeric cup includes an open end and a closed end, wherein the open end is affixed to the cup frame, wherein the flexible polymeric cup is adapted to be reconfigured during implantation in a bodily lumen from a pre-deployed state to an everted state, and wherein the flexible polymeric cup in the everted state is adapted to occlude the lumen.

In various implementations the method of making an implantable occlusion device may further comprise forming the shape memory wire into a coil, wherein the coil may have an overall outside diameter and a coil length; elongating the coil, wherein the elongated coil may have an elongated coil length that is greater than the coil length, and wherein the elongated coil may have an elongated coil diameter that is less than the overall outside diameter of the coil; fitting a flexible polymeric tube over the elongated coil, the flexible polymeric tube may have an inside diameter that is less than the overall outside diameter of the coil; and allowing the elongated coil to recoil to a contracted length, wherein the contracted length may be less than the elongated coil length, thereby causing the flexible polymeric tube to form an irregular shape useful for occlusion; the method of making an implantable occlusion device may further comprise, prior to allowing the elongated coil to recoil, incising the flexible polymeric tube to create a fringe portion along at least a portion of a length of the flexible polymeric tube; the method of making an implantable occlusion device may further comprise forming the shape memory wire into a coil, wherein the coil may have an overall outside diameter; elongating the coil, thereby increasing a length of the coil to an elongated length and reducing the overall outside diameter of the coil; wrapping a flexible polymeric material onto the elongated coil, wherein the elongated coil may be substantially covered by the flexible polymeric material, and wherein portions of the flexible polymeric material may not be in direct contact with the elongated coil; and allowing the elongated coil to recoil to a contracted length, wherein the contracted length may be less than the elongated length, thereby causing the flexible polymeric material to form an irregular shape useful for occlusion; and the method of making an implantable occlusion device may further comprise, prior to allowing the elongated coil to recoil, incising the flexible polymeric material to create a fringe portion along at least a portion of a length of the flexible polymeric material.

Other aspects, features, and advantages will be apparent from the description, the drawings, and the claims.

BRIEF DESCRIPTION OF THE DRAWINGS

FIGS. 10A-10D illustrate an example deployment process of an example cup-shaped occlusion device in a bodily vessel.

Like reference symbols in the various drawings indicate like elements.

DETAILED DESCRIPTION

Medical devices used to occlude a bodily lumen, organ, vessel, or cavity, as well as methods for making the devices and for treating a subject using the devices are provided in this disclosure. In general, the occlusion devices include one or more elongate members (hereinafter a "wire" or "wires") combined with flexible membranous materials. The occlusion devices utilize the wires and flexible membranous materials in various configurations. The wires of the occlusion devices can define the shape of the occlusion devices, and prevent or inhibit migration of the occlusion devices from a desired bodily location. The flexible membranous materials of the occlusion devices may be treated to enhance, for example, their thrombogenicity and epithelialization properties.

Figure 1:
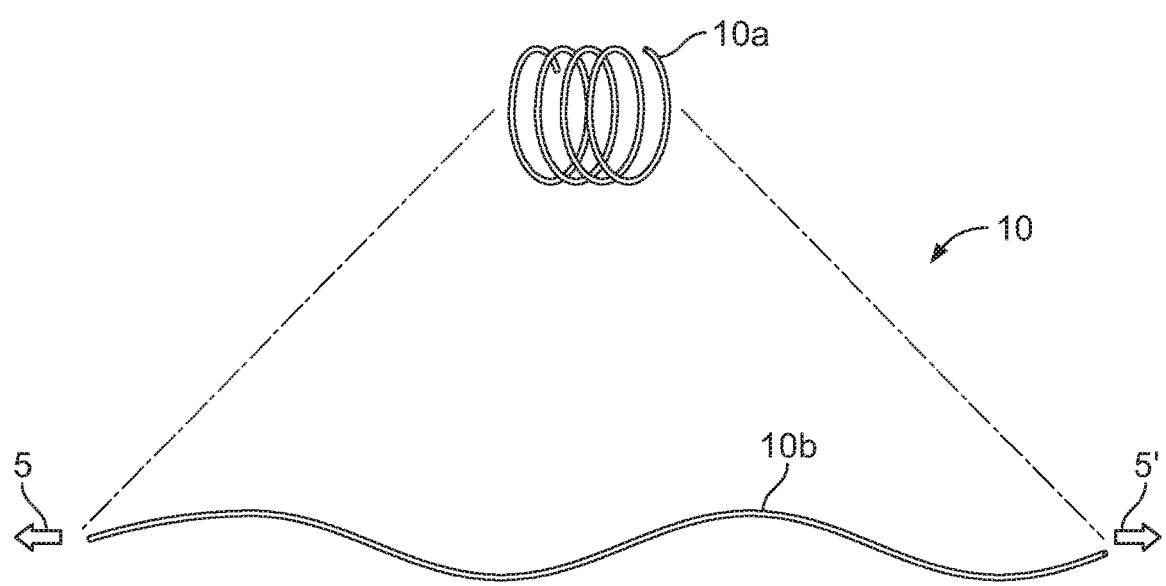
FIG. 1 depicts an elongate member of an example occlusion device in a relaxed configuration and a low-profile configuration.

With reference to FIG. 1, a wire 10 of an example occlusion device is depicted in a relaxed configuration 10a and a low-profile delivery configuration 10b. In general, wire 10 is a component of an example occlusion device embodiment that also includes a flexible membranous material (see, e.g., FIG. 3).

In some embodiments, the occlusion devices provided herein include one or more such wires. The wires of the occlusion devices may exhibit, for example, beneficial fatigue resistance and elastic properties. In some embodiments, the occlusion devices are constructed of one or more wires that have elastic and/or shape memory properties that allow the devices to be configured in a low-profile configuration for transcatheter delivery or thoracoscopic delivery, and to self-expand to an operative size and configuration once positioned at a desired target site within a bodily lumen, cavity, vessel, or organ.

The wires can comprise a variety of materials. The wires may be elastomeric, metallic, spring wires, shape memory alloy wires, super-elastic alloy wires, or combinations and sub-combinations thereof, to name a few general examples. In fact, any type of wire that is suitably biocompatible, flexible, and resilient can generally be used for the occlusion devices provided herein. For example, the wires can comprise nitinol (NiTi), L605 steel, stainless steel, polymeric materials, or any other appropriate biocompatible material, including combinations and sub-combinations of materials. In some embodiments, bioresorbable or bioabsorbable materials may be used, including, for example, a bioresorbable or bioabsorbable polymer. In some such embodiments, the wire may eventually dissolve, while leaving thrombus or cellular matter in its place. In some embodiments, the wire is fully or partially coated to stimulate a biological reaction.

It should be clear that suitable wire materials include a variety of metallic shape memory materials and super-elastic alloys. Shape memory refers to the ability of a material to revert to an originally memorized shape after plastic deformation by heating it above a critical temperature. Superelasticity refers to the ability of a material to deform under strain to a very large degree, without having this deformation become permanent. For example, the shape memory materials included in some embodiments are able to withstand a significant amount of bending and flexing and yet return to its original form without deformation. Some metallic shape memory materials used in the occlusion devices are described in U.S. Pat. Nos. 3,174,851; 3,351,463; and 3,753,700, which are hereby incorporated by reference in their entireties. Suitable shape memory materials include various stainless steels which have been physically, chemically, and otherwise treated to produce high springiness, metal alloys such as cobalt chrome alloys (e.g., ELGILOY™), platinum/tungsten alloys, and the NiTi alloys.

The super-elastic properties of NiTi make it a suitable material for the wires of some embodiments of the occlusion devices provided herein. NiTi wire can be heat-set into a desired shape such that the NiTi wire will tend to self-expand into the desired shape when it is deployed from a delivery sheath into a bodily lumen, cavity, vessel or organ.

The wire can be treated in various ways to increase the radiopacity of the wire for enhanced radiographic visualization. In some embodiments, the wire is at least partially a drawn-filled type of NiTi containing a different material at the core, such as a material with enhanced radiopacity. In some embodiments, the wire has a radiopaque cladding or plating at least on portions of the wire.

In some embodiments, the diameter or thickness of the wires are about 0.1 mm to 1.50 mm, but in other embodiments wires having smaller or larger diameters are used. In some embodiments, the wires have a diameter of about 0.25 mm. It should be clear that wires of any suitable size or diameter can be used.

In some embodiments, each of the one or more wires of the device have the same diameter. In some embodiments, each of the one or more wires of the device have different diameters. In some embodiments, the one or more wires have a consistent diameter along the length of the wire. In some embodiments, one or more portions of the one or more wires are diametrically tapered or otherwise inconsistent in diameter. In some embodiments, the wires may be formed using a center-less grinding technique, such that the diameter of the wire varies along the length of the wire. The wires may have a round cross-sectional shape or may have a cross-sectional shape that is not round, such as a rectangle or other polygon. Examples of other cross-sectional shapes that the wires may have include a square, oval, rectangle, triangle, D-shape, trapezoid, or irregular cross-sectional shape formed by a braided or stranded construct. In some embodiments, the one or more wires of an occlusion device may include flat wires. In some embodiments, a combination of various types of wires are used in an occlusion device. While in some embodiments the one or more wires of the device each have the same cross-sectional shape, in some embodiments, at least one wire has a different cross-sectional shape than one or more of the other wires.

In some embodiments, one or more wires of the occlusion devices provided herein may include one or more fixation elements (e.g., anchors, barbs, protrusions, and/or penetrating members). In some embodiments, such fixation elements advantageously reduce or inhibit in situ migration of the occlusion devices after deployment to a target site within a bodily lumen, cavity, vessel or organ.

Referring to FIG. 1, wire 10 is shown in a relaxed configuration 10a and a low-profile delivery configuration 10b. The relaxed configuration 10a is the natural configuration that wire 10 seeks when it is not exposed to external forces. The low-profile delivery configuration 10b is the configuration that wire 10 assumes when it is exposed to certain external forces, such as the equal and opposite stretching forces 5 and 5'. While the low-profile delivery configuration 10b is generally linear, in some embodiments the configuration includes some undulations.

In some embodiments, a heat-set process is used to make wire 10 have the relaxed configuration 10a. For example, in some embodiments wire 10 is a NiTi wire that has been heat-set into a helically coiled configuration corresponding to relaxed configuration 10a. In some implementations, the wire 10 is wound onto a suitable mandrel and then heated to heat-set the wire 10 in a coiled configuration as substantially defined by the mandrel geometry. While wire 10 is depicted in its relaxed configuration 10a as generally helical, as described further below in reference to FIGS. 6A-6F, a wide variety of coil configurations are envisioned. In some embodiments, wire 10 is plastically deformed into the coiled relaxed configuration 10a. In some embodiments, wire 10 is molded into the coiled relaxed configuration 10a. In sum, any suitable method for configuring a wire in a coiled configuration can be utilized.

The delivery configuration 10b can be attained by applying equal and opposite stretching forces 5 and 5' to relaxed configuration 10a. Wire 10 is configured in a substantially linear shape while in the low-profile delivery configuration 10b. The delivery configuration 10b is suitable for delivering the wire 10 to a desired target site in a bodily lumen, cavity, vessel or organ using a delivery catheter or sheath. In general, the delivery configurations of the occlusion devices provided herein are low-profile configurations, so as to enable the use of small diameter delivery catheters or sheaths. To illustrate, as FIG. 1 shows, the approximately linear low-profile delivery configuration 10b has a much smaller radial profile than the coiled relaxed configuration 10a.

Figure 2:
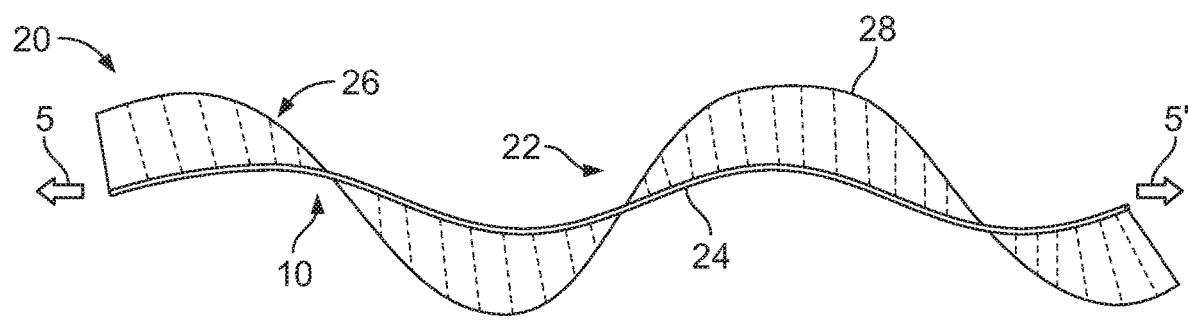
FIG. 2 depicts an example occlusion device in a low-profile configuration.

With reference to FIG. 2, an example occlusion device 20 includes a wire 10 (not visible) covered by a membranous material 22. The example occlusion device 20 is depicted in a low-profile delivery configuration. That is, example occlusion device 20 is in a low-profile configuration (by virtue of stretching forces 5 and 5') as used when delivering example occlusion device 20 via a delivery catheter or sheath. Upon emergence from the delivery catheter or sheath, the example occlusion device 20 would seek a relaxed configuration analogous to the coiled relaxed configuration 10a of FIG. 1 (or another configuration depending on the type of occlusion device).

The flexible membranous materials used for the occlusion devices provided herein may have pores that are sized to substantially (or, in some embodiments completely) prevent the passage of bodily fluids and emboli through the membranous materials. In some embodiments, the membranous materials have a microporous structure that provides a tissue ingrowth scaffold for durable occlusion and supplemental anchoring strength of the occlusion devices in a bodily lumen, cavity, vessel or organ. In some embodiments, the membranous materials are configured such that the inhibition of fluid passage through the membranous sheet material is immediate and does not rely on a thrombotic process. In some embodiments, the membranous materials initiate a cascade of thrombosis, such that the final occlusive effect is attained by a combination of inhibition of fluid passage by the membranous material and the blood's own natural thrombetic process.

In general, the flexible membranous materials can comprise any suitable biocompatible material. Suitable materials include, but are not limited to, porous or non-porous synthetic polymers such as polyethylene, polypropylene, polyurethane, polyglycolic acid, polyesters, polyamides, polyesters such as polyethylene terephthalate, polyaramids, polyfluorocarbons such as fluorinated ethylene propylene (FEP), perfluorinated alkoxy (PFA), polytetrafluoroethylene (PTFE), and expanded polytetrafluoroethylene (ePTFE), and their mixtures, blends and copolymers. ePTFE materials are described in U.S. Pat. Nos. 3,953,566 and 4,187,390 the entireties of which are hereby incorporated by reference. A suitable ePTFE polymeric sheet material is taught by U.S. Pat. No. 5,814,405, also hereby incorporated by reference in its entirety. In some embodiments, the membranous materials are bioresorbable or bioabsorbable materials, such as bioresorbable or bioabsorbable polymers. In some embodiments, the membranous materials are formed of a copolymer. In some embodiments, a first portion of the membranous material of an occlusion device is formed of a first material and a second portion of the membranous sheet material of the device is formed of a second material. For example, the portion of the membranous material that covers a wire of the device may be formed of a first material, and the remaining portions of the membranous sheet material of the device may be formed of a second material. In some embodiments, three or more types of membranous materials are used on a single occlusion device.

Any suitable type of construction of the membranous material can be used for the occlusion devices provided herein. In some embodiments, the membranous material has a knitted construction. In some embodiments, the membranous material has a woven construction. In some embodiments, the membranous material has a mesh construction. In some embodiments, the membranous material has a film construction. In some embodiments, a combination of construction types are included in a single occlusion device. In some embodiments, multiple layers of dissimilar types of membranous materials and/or types of constructions are included in a single occlusion device. In some embodiments, the membranous materials include hairs or filaments of membranous material attached to the surface of the membranous material. In some such embodiments, the hairs or filaments can increase the thrombogenicity of the membranous material.

In some embodiments, the membranous materials are made in sheet or strip form. In some embodiments, the membranous materials are subsequently wound, knitted or woven into a tube form. In some embodiments, the membranous materials are made in filament or thread form, and are subsequently wound, knitted or woven into a sheet, strip or tube form. In some embodiments, the membranous materials are extruded as a sheet, strip, or tube form.

Some embodiments of the membranous materials are made by a spinning process. Some embodiments of spun membranous materials are made in sheet form. Some embodiments of spun membranous materials are made in tube form, for example by spinning materials onto a mandrel. Various spinning processes can be used, including: wet spinning, dry spinning, melt spinning, extrusion spinning, direct spinning, gel spinning, and electro-spinning, to name a few examples. In some embodiments, spinning processes provide membranous materials that include micro or nano filaments.

In some embodiments, the membranous materials used in the occlusion devices provided herein are modified by one or more chemical or physical processes that enhance certain properties of the membranous materials. For example, in some embodiments, a hydrophilic coating is applied to the membranous sheet materials to improve the wettability and echo translucency of the membranous materials. In some embodiments the membranous materials are modified with chemical moieties that promote one or more of endothelial cell attachment, endothelial cell migration, endothelial cell proliferation, and resistance to or promotion of thrombosis. In some embodiments the membranous materials are modified with one or more covalently attached drug substances (e.g., heparin, antibiotics, and the like) or impregnated with the one or more drug substances. The drug substances can be released in situ to promote wound healing, reduce tissue inflammation, reduce or inhibit infections, and to promote various other therapeutic treatments and outcomes. In some embodiments the drug substance is a corticosteroid, a human growth factor, an anti-mitotic agent, an antithrombotic agent, a stem cell material, or dexamethasone sodium phosphate, to name some examples. Coatings and treatments may be applied before or after the membranous material is affixed or disposed on the wire of the occlusion devices. Additionally, one or both sides of the membranous material may be coated. In some embodiments, certain coatings and/or treatments are applied to the membranous material located on some portions of an occlusion device, and other coatings and/or treatments are applied to the membranous material located on other portions of the occlusion devices. In some embodiments, a combination of multiple coatings and/or treatments are applied to the membranous materials. In some embodiments, certain portions of the device are left uncoated and/or untreated.

In some embodiments, the membranous materials used for the occlusion devices herein are an elastomeric film material. That is, in some embodiments the membranous sheet materials can stretch and rebound to accommodate the movement of the wires during reconfiguration of the occlusion devices, such as between the low-profile and the relaxed configurations. Such elasticity of the membranous materials can, in some embodiments, advantageously facilitate the reconfiguration of the occlusion devices without ancillary stress relief measures (such as incisions to the membranous material).

Still referring to FIG. 2, the membranous material 22 is applied to the wire 10 of the example occlusion device 20. In some embodiments, the membranous material 22 is applied to the wire 10 so that the membranous material 22 creates a wire sleeve portion and a fringe 26 portion. For example, in some embodiments membranous material 22 is an elongate strip of material that is folded around the wire 10 to form the wire sleeve 24, and the length-wise free ends of the strip are affixed to each other to form the fringe 26. In some embodiments, the free ends of the membranous material 22 are affixed to each other using a fluorinated ethylene propylene (FEP) coating or film. In some embodiments, the free ends of the membranous material 22 are affixed to each other by stitching, welding/bonding, using various biocompatible adhesives, or by other suitable methods or a combination of methods. By folding the strip of membranous material 22 over the wire 10, the wire 10 can be fully or partially covered by the membranous material 22. In some embodiments, a portion of the wire 10 can be exposed, i.e., a portion of the wire 10 may not be covered by membranous material 22. For example, in some embodiments, the ends of the wire 10 are exposed.

In some embodiments, the membranous material 22 is applied to the wire 10 by winding it around the wire 10. In some embodiments the diameter of the wound membranous material 22 is greater than the diameter of the wire 10 so that a fringe 26 can be formed. The fringe 26 can be formed by flattening the excess membranous material (material that remains after covering the wire) and affixing the flattened layers to each other.

In some embodiments, the wire 10 and the fringe 26 are about the same length (with the length being measured along the axis of the wire 10). In some embodiments, the fringe 26 extends past the ends of the wire 10 so that the fringe 26 is longer than the wire 10. In some embodiments, the fringe 26 extends past the wire 10 on just one end of the wire 10. In some embodiments, the fringe 26 extends past the wire 10 on both ends of the wire 10.

In some embodiments, the wire 10 is not located along an edge of the membranous material 22. In some embodiments, the wire 10 is positioned about in the middle of one or more strips of membranous material 22. In some such embodiments, two or more fringe 26 portions are created—with the wire 10 in between the fringe portions. While in some embodiments, the two or more fringe 26 portions have individual fringes 28 of approximately the same length, in some embodiments the two or more fringe 26 portions have individual fringes 28 of different lengths.

In some embodiments, the wire 10 is positioned off-center on (or between) one or more strips of membranous material 22 (but not at an edge). In some such embodiments, two or more fringe 26 portions with unequal transverse lengths are formed. In some embodiments, the wire 10 is positioned on or between layers of membranous strips and the wire 10 has a pattern that is not substantially linear. In some such embodiments, two or more fringe 26 portions with variable and unequal lengths are formed.

In some embodiments, the wire 10 has an adhesive coating to assist in the application of the membranous material 22 to the wire 10, and to affix the wire 10 to the membranous material 22. For example, in some embodiments the adhesive on the wire 10 is FEP, applied by a powder coating process. In some embodiments, other biocompatible adhesives are used on the wire 10 in addition to or in place of FEP. The adhesive on the wire 10 can cover the entire wire 10, or be in certain discrete locations on the wire 10.

In some embodiments, the membranous material 22 has adhesive properties. In some embodiments, a FEP coating or FEP film layer is applied to all or portions of the membranous material 22. In some embodiments, the adhesives are heat-activated. In some embodiments, various other biocompatible adhesives are incorporated within or on the surface of the membranous material 22. The adhesives can assist in attaching the membranous material 22 to the wire 10, as well as in adhering layers of the membranous material 22 to each other.

In addition to or instead of adhesives, any other suitable method for affixing the wire 10 to the membranous material 22 can be used. For example, in some embodiments, the wire 10 is affixed to the membranous material 22 using stitching. In some embodiments, the wire 10 has a textured surface, or textured surface portions, to create a grip between the wire 10 and the membranous material 22. In some embodiments, the wire 10 has barbs or protrusions that penetrate the membranous material 22 to affix the two together. In some embodiments, the wire 10 has portions with a larger cross-sectional profile to create an interference fit between the wire 10 and the sleeve 24 at certain locations. In some embodiments, the fit between the entire length of the wire 10 and the sleeve 24 is an interference fit. In some embodiments, the fit between the entire length of the wire 10 and the wire sleeve 24 is a line-to-line fit.

A variety of other relationships between the wire 10 and the membranous material 22 are also envisioned. For example, in some embodiments the dimensional fit between the wire 10 and the wire sleeve 24 of the membranous material 22 is a slip fit along the entire length of the wire 10. In some embodiments, the wire 10 is not affixed to the membranous material 22. In some embodiments, ends of the wire 10 are doubled-over and crimped to pinch and capture the membranous material 22. Alternatively, the membranous material 22 can extend beyond the end of wire 10.

In some embodiments, the wire 10 is affixed to the membranous material 22 by weaving the wire 10 through the membranous material 22. In some such embodiments, one or more layers of membranous sheet material 22 can be included.

In some embodiments of the occlusion devices provided herein, one or more radiopaque markers are included. The radiopaque markers can assist with the radiographic visualization of the occlusion devices—which can be beneficial during the implantation procedure. In some embodiments, the radiopaque markers are affixed at one or more locations on the membranous material. In some embodiments, the radiopaque markers are integral portions of the membranous material. In some embodiments, the radiopaque markers are affixed at one or more locations on the one or more wires. In some embodiments, the radiopaque markers are integral portions of the one or more wires. In some embodiments, the radiopaque markers are located at one or more locations on both the membranous sheet and the one or more wires. In some embodiments, the membranous material is wetted with contrast solution prior to deployment to provide enhanced radiopacity during the deployment procedure.

In some embodiments, the fringe 26 portion(s) are initially a material that is non-integral to the membranous material elsewhere on an occlusion device (e.g., sleeve 24). In some such embodiments, the fringe 26 can be, for example, affixed to the other membranous material as a step in the process of manufacturing an occlusion device. The fringe 26 can be affixed to the membranous material using any suitable method such as by using adhesives, stitching, welding, bonding, and the like. In some such embodiments, the fringe 26 can be a dissimilar material (in comparison to the membranous material elsewhere on the occlusion device). In some embodiments, the material of the fringe 26 can be selected to provide desirable properties and features particularly suited for individual fringes 28, whereas the membranous material elsewhere on the device can be selected to provide properties and features particularly suited for those locations. In some embodiments, the individual fringes 28 are made to be stiffer than the membranous material used elsewhere on the device (to name one example). In some embodiments, non-integral membranous material is the same type of material as used elsewhere on the occlusion device 20.

Still referring to FIG. 2, individual fringes 28 can be formed by incising or cutting the fringe 26 portion(s) of the membranous material 22 (as represented by the transverse cut-lines projecting from the wire sleeve 24). The cuts to the fringe 26 create multiple individual fringes 28 of membranous material. In some embodiments, the fringe 26 cuts are made approximately in a radial or orthogonal direction in relation to the wire 10. In some embodiments, the fringe 26 cuts are made at non-orthogonal angles in relation to the wire 10. In some embodiments, a combination of orthogonal and non-orthogonal cuts (in relation to the wire 10) are used. Therefore, in some embodiments the individual fringes 28 are generally rectangular-shaped. In some embodiments, the individual fringes 28 are triangular or shaped like trapezoids. In some embodiments, the individual fringes 28 are irregularly shaped. In some embodiments, the individual fringes 28 of an occlusion device are a variety of such shapes and irregular shapes.

Figure 3:
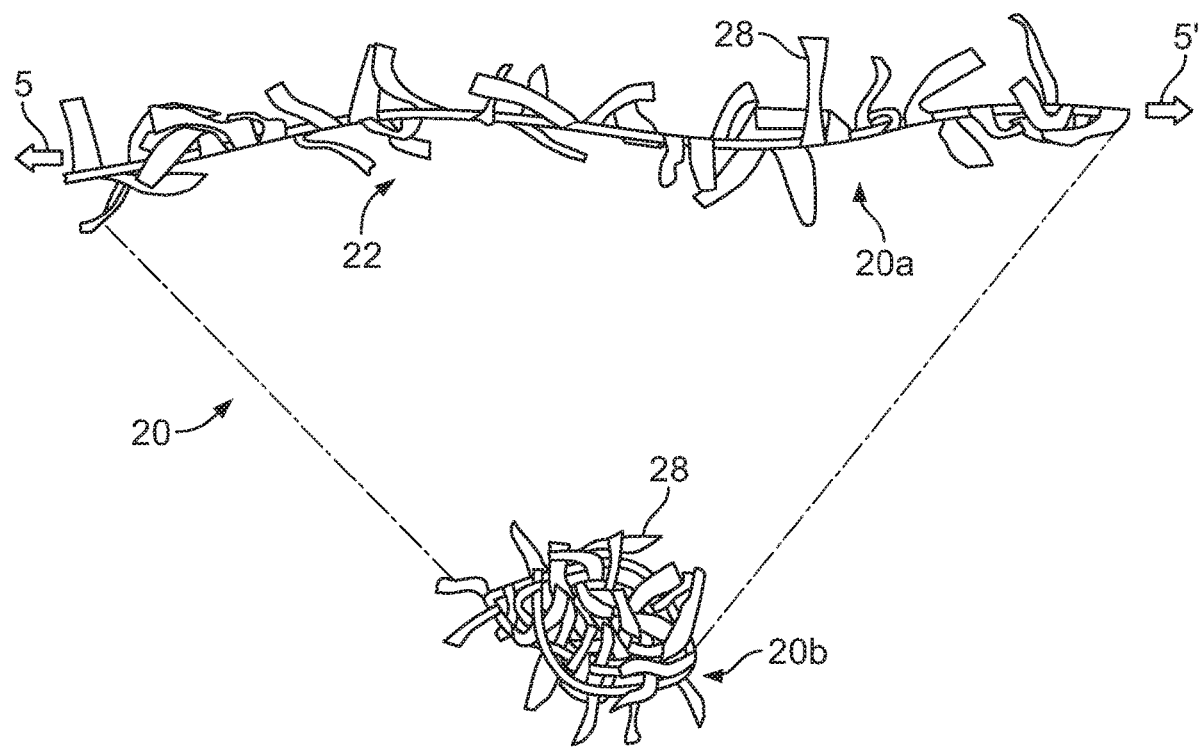
FIG. 3 depicts an example occlusion device in a low-profile configuration and a relaxed configuration.

With reference to FIG. 3, the example occlusion device 20 is illustrated in a low-profile delivery configuration 20a and a relaxed configuration 20b (depending on presence or absence of stretch forces 5 and 5'). The multiple individual fringes 28 are now distinctly visible. The individual fringes 28 can also be considered as membranous strips, strands, ribbons, fingers, filaments, projections, bristles, free ends, frayed portions, hairs, and the like. In some embodiments, the individual fringes 28 perform various beneficial functions for occlusion devices. For example, when the occlusion device 20 is implanted in a bodily lumen, cavity, vessel, or organ, the individual fringes 28 may provide fluid flow obstructions, cavity filler material, tissue ingrowth scaffolding, thrombogenicity elements, and the like. In addition, in some embodiments the individual fringes 28 provide a stress relief function that is beneficial when the wire is transitioned between its low-profile delivery and its relaxed configurations. That is, the individual fringes 28 can tend to reduce some external forces that the membranous sheet 22 may otherwise exert on the wire 10 as the wire changes shapes. When occlusion device 20 is implanted in a bodily lumen, cavity, vessel, or organ, occlusion device 20 approximately takes on the configuration of relaxed configuration 20b.

The individual fringes of the occlusion devices provided herein can have any suitable length. In some embodiments, the fringes are about 2.50 mm to 12.70 mm long, but in other embodiments fringes with shorter or longer lengths are used. For example, embodiments using spun membranous materials can include fringes, hairs, or filaments in the nano range. It should be understood that fringes of any suitable length are envisioned within the scope of this document. In some embodiments, the fringes have a substantially consistent length on the entire occlusion device. In some embodiments, the fringes have variable lengths at different locations on the occlusion device. For example, in some embodiments the fringes are longer near the middle of the occlusion device than at the ends of the occlusion device. In some embodiments the fringes are shorter near the middle of the occlusion device than at the ends of the occlusion device. In some embodiments, the lengths of the fringes vary approximately according to a pattern (e.g., a sinusoidal wave or other pattern). In some embodiments, the lengths of the fringes are randomly variable.

Individual fringes of the occlusion devices provided herein can be formed to have a variety of widths or diameters. In some embodiments, the widths or diameters of the fringes are about 0.50 mm to 2.50 mm, but in other embodiments fringes having wider or narrower widths or diameters are used. It should be understood that fringes of any suitable width or diameter are envisioned within the scope of this document. In some embodiments, the fringes have a substantially consistent width or diameter on the entire occlusion device. In some embodiments, the fringes have variable widths or diameters at different locations on the occlusion device. For example, in some embodiments the fringes are wider near the middle of the length of the occlusion device than at the ends of the occlusion device. In some embodiments, the fringes are narrower near the middle of the length of the occlusion device than at the ends of the occlusion device. In some embodiments, the widths or diameters of the fringes vary approximately according to a pattern along the length of the wire. In some embodiments, the widths or diameters of the fringes are randomly variable.

Figure 4:
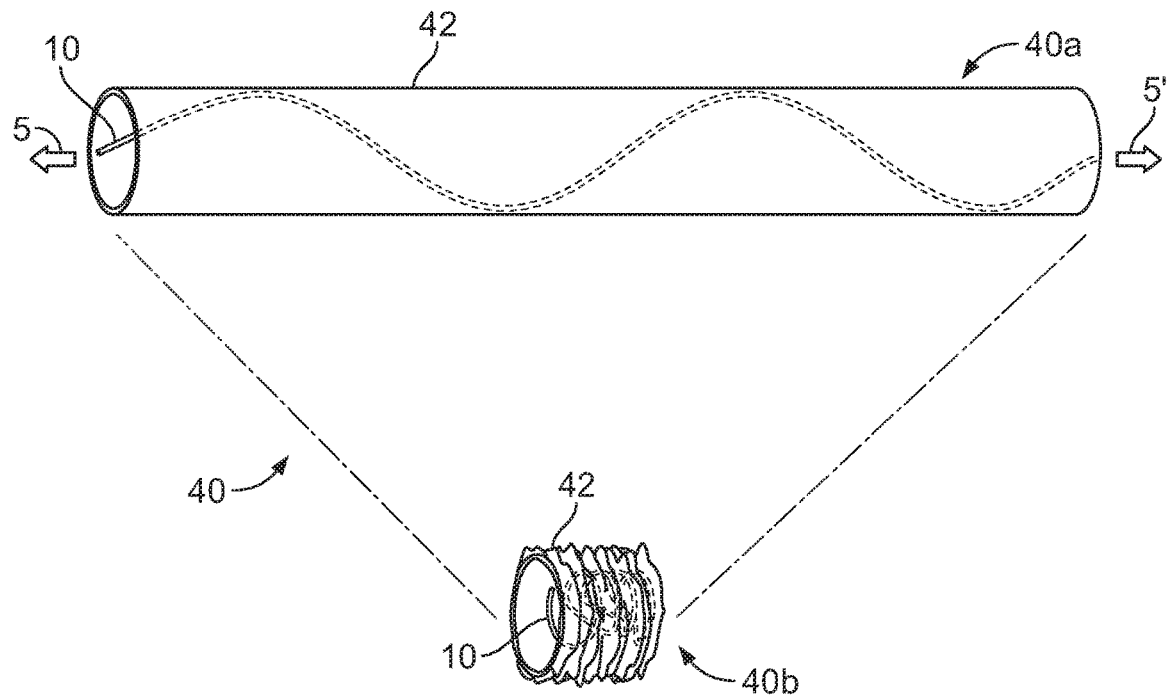
FIG. 4 depicts an example occlusion device in a low-profile configuration and a relaxed configuration.

With reference to FIG. 4, an example occlusion device 40 is illustrated in its delivery configuration 40a and its relaxed configuration 40b. The example occlusion device 40 includes a membranous tube 42 and one or more wires 10. The natural relaxed (or shape-memory) configuration of wire 10 is a coiled configuration (see, e.g., FIGS. 6A-6F). Therefore, for occlusion device 40 to be in the delivery configuration 40a requires the application of external force(s), such as stretching forces 5 and 5'. The elimination or substantial reduction of stretching forces 5 and 5' allows the occlusion device 40 to coil into its relaxed configuration 40b. Configuration 40b is approximately the configuration that the occlusion device 40 will assume when it is implanted in a bodily lumen, cavity, vessel, or organ.

The materials and methods of construction of occlusion device 40 are generally analogous to the materials and methods of construction of occlusion device 20 described above. For example, membranous tube 42 can be constructed using any of the materials, material treatments, and manufacturing methods described above in regard to membranous materials and tubes. In addition, wire 10 can be constructed using any of the materials, material treatments, and manufacturing methods described above. Further, the membranous tube 42 and wire 10 can be affixed to each other using any of the methods described above for affixing a membranous sheet to a wire.

However, differences exist between occlusion device 40 illustrated in FIG. 4 and occlusion device 20 described above. For example, in some embodiments the diametric size difference between the membranous tube 42 and wire 10 is greater than the diametric size difference between sleeve 24 and the wire 10 of occlusion device 20. In some embodiments, the size difference between the membranous tube 42 and wire 10 allows the wire 10 to take the form of a helix within the membranous tube 42 when the occlusion device 40 is in the delivery configuration 40a. In some embodiments, the wire 10 takes non-linear forms other than a helix within the membranous tube 42, when the occlusion device 40 is in the delivery configuration 40a. In some embodiments, the wire 10 is substantially linear within the membranous tube 42.

Further, in some embodiments example occlusion device 40 does not include fringes like occlusion device 20. Rather, the membranous tube 42 becomes bunched or gathered together when the occlusion device 40 is configured in its relaxed configuration 40b. The membranous tube 42 in its bunched together arrangement can provide the occlusive properties as well as other properties that are desirable for an occlusion device.

Figure 5:
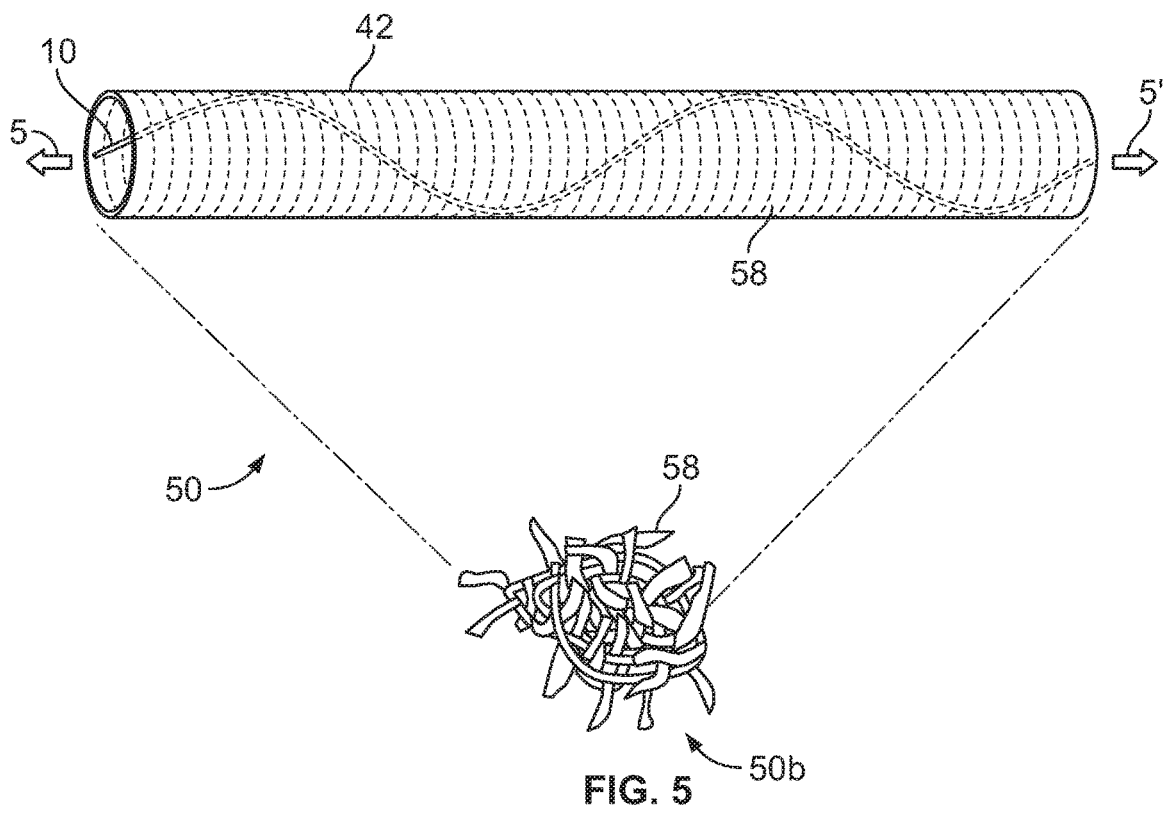
FIG. 5 depicts an example occlusion device in a low-profile configuration and a relaxed configuration.

With reference to FIG. 5, another example occlusion device 50 is illustrated in its delivery configuration 50a and its relaxed configuration 50b. The example occlusion device 50 includes a membranous tube 52 and one or more wires 10. The relaxed (or shape-memory) configuration of wire 10 is a coiled configuration (see, e.g., FIGS. 6A-6F). Therefore, for occlusion device 50 to be in the delivery configuration 50a requires the application of external force(s), such as stretching forces 5 and 5'. The elimination or reduction of stretching forces 5 and 5' allows the occlusion device 50 to coil into its relaxed configuration 50b. Configuration 50b is approximately the configuration that the occlusion device 50 will assume when it is implanted in a bodily lumen, cavity, vessel, or organ.

Example occlusion device 50 includes the features of example occlusion device 40 described above. In addition, occlusion device 50 includes individual fringes 58. In general, the individual fringes 58 can be constructed and can include the features described above in reference to fringes 28.

In some embodiments, the individual fringes 58 can be formed by making multiple transverse cuts to the membranous tube 52 (fringe cut-lines are represented by the substantially radial lines shown in delivery configuration 50a). In some embodiments, individual cuts are not made fully around the circumference of the membranous tube 52. That is, an individual cut does not fully sever a portion of the membranous tube 52 so as to create multiple tubes. For example, in some embodiments the portions of the membranous tubes 52 adjacent to the wire 10 are not cut.

When occlusion device 50 is allowed to assume its relaxed configuration 50a, the individual fringes 58 can project from the coiled wire 10 so as to create a larger profile as compared to similar occlusion devices without fringes 58. The larger profile can be advantageous for certain implementations of an occlusion device.

FIGS. 6A-6F illustrate example wire coil shape embodiments. The coil shapes shown are approximately in their relaxed configurations. However, in some examples the coils are enlarged or elongated to assist with the visualization of the configuration of the coil shape. The example coil shapes provided have shapes and properties that can be mixed and matched in any combination to provide the desired shape and properties of the wires for various embodiments of the occlusion devices provided herein.

Figure 6A:
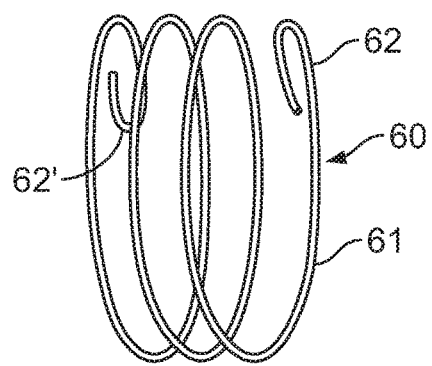
FIGS. 6A-6F illustrate examples of wire coil configurations for use in occlusion devices.

FIG. 6A illustrates a generally helical coil 60 that is similar to the relaxed configuration 10a of FIG. 1. The generally helical coil 60 is made from wire 61. The generally helical coil 60 includes ends 62 and 62'. The ends 62 and 62' are made by doubling over the wire 61. This has the effect of making ends 62 and 62' more bluntly-shaped than the ends 62 and 62' would be if the wire was not doubled over. Such blunt ends are desirable in some occlusion device embodiments. In some embodiments, the ends of the wire can be made blunt by other techniques, such as by adding bulbous tips to the ends of the wire.

Figure 6B:
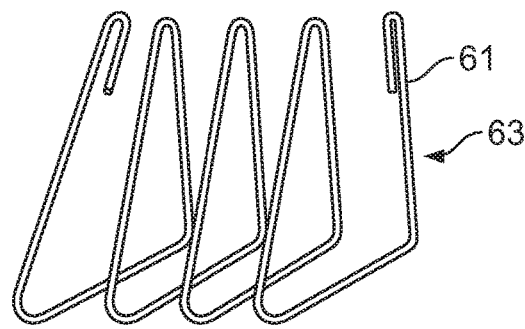

FIG. 6B illustrates a triangular coil 63. In some embodiments, the coils such as triangular coil 63 (and the others described herein) can be formed by winding the wire 61 onto a mandrel that defines the general shape of the coil being made. For example, triangular coil 63 can be formed by wrapping the wire 61 in a triangular pattern on a suitable mandrel. In some embodiments, a super-elastic shape memory alloy wire can be used, and the wire can be heat-set into the pattern it acquired as a result of being wound onto a mandrel.

Figure 6C:
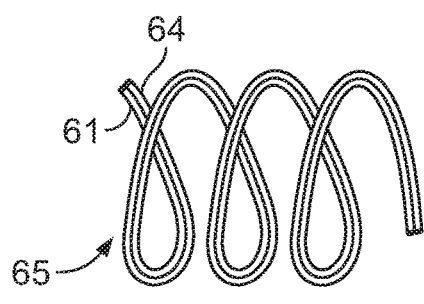

FIG. 6C illustrates a double coil 65. Double coil 65 includes wires 61 and 64 that are wound on the same axis, in the same direction, and using the same pitch. In the embodiment shown, the wires 61 and 64 operate in conjunction with each other like two strands of a stranded wire. While double coil 65 has side-by-side wires 61 and 64, in some embodiments the wires can be twisted together or otherwise entangled with each other. In some embodiments, the wires 61 and 64 can be incongruent, have different pitches, or be on different axes. In some embodiments, such multiple stranded constructions can provide a coil with enhanced capabilities to be elastically deformed, while also providing a stronger bias to seek the relaxed configuration as compared to a single wire. In some embodiments, more than two wires are used in a coil embodiment.

Figure 6D:
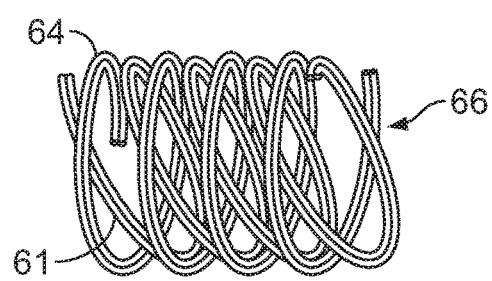

FIG. 6D illustrates another coil 66 that is made of more than one wire. Coil 66 includes wires 61 and 64. In this embodiment, one wire is wound using a right-handed helix and the other wire is wound using a left-handed helix. Both are wound on the same axis. In some embodiments, the wires can be wound on different axes. In some embodiments, the wires 61 and/or 64 comprise multiple stranded wires such as side-by-side wires as shown.

Figure 6E:
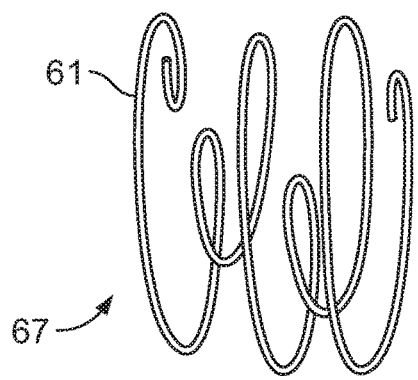

FIG. 6E illustrates a randomized coil 67. In this embodiment, the turns of wire 61 are wound at various coil diameters, axes, pitches, and so on. This randomized configuration can provide enhanced occlusion in some implementations.

Figure 6F:
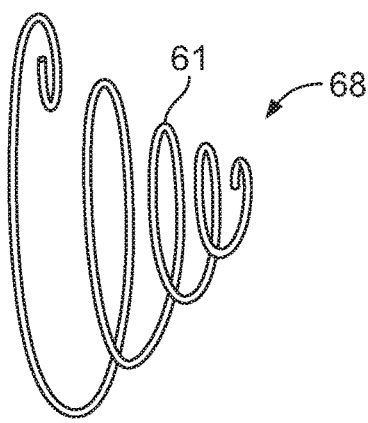

FIG. 6F illustrates a conical coil 68. In this embodiment, the wire 61 is wound with an increasingly larger outer diameter for each coil turn, while on the same axis. This conical coil 68 configuration can provide enhanced occlusion at the center area of the occlusion device in some implementations.

Figure 7:
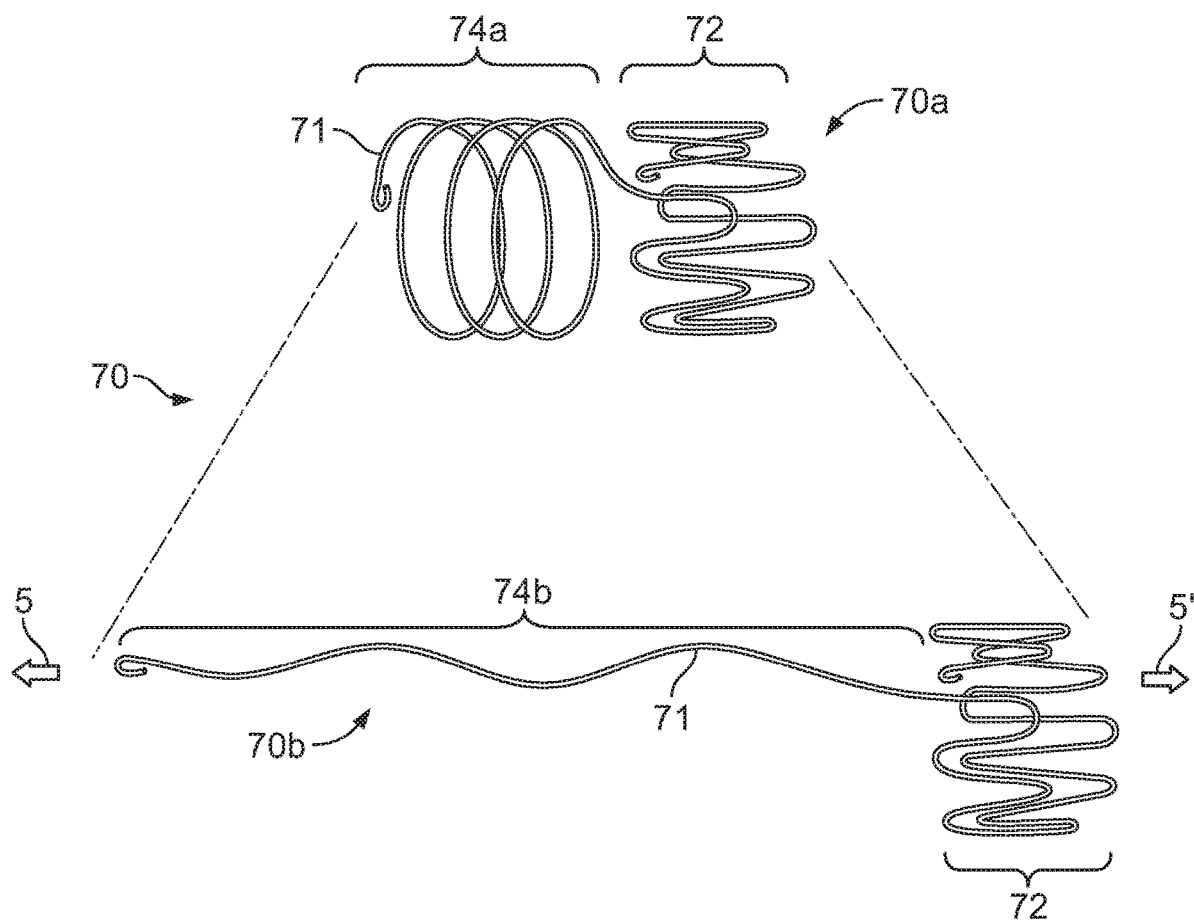
FIG. 7 depicts an elongate member frame of an example cup-shaped occlusion device in a relaxed configuration and a low-profile configuration.

With reference to FIG. 7, a wire frame 70 of an example cup-shaped occluder embodiment is depicted in a relaxed configuration 70a and a delivery configuration 70b (again depending on presence or absence of stretch forces 5 and 5'). In general, wire frame 70 is a component of an example occlusion device embodiment that also includes a membranous material (see, e.g., FIGS. 8 and 9).

In the illustrated embodiment the wire frame 70 includes two (2) portions. The first portion is a cup frame 72. The second portion is a coil portion 74 (shown in a relaxed configuration 74a and a low-profile configuration 74b). In some embodiments, the wire frame 70 is made of a single wire 71. In some embodiments, the wire frame 70 is made of two or more wires. When two or more wires are used, they may or may not be coupled together. In some embodiments, the wire frame includes three or more portions. The wire 71 has the properties and features of the wires described above.

In some embodiments, the wire frame 70 includes the cup frame 72 portion, but no coil portion 74 is included. In some such embodiments, the occluder device embodiment includes a membranous cup portion and does not include an additional membranous occluder portion (i.e., portion 74 of FIG. 8 and portion 96 of FIG. 9 is not included).

The cup frame 72 is generally shaped like a wire-framed open cylinder. In some embodiments, the cup frame 72 can be formed by bending a wire 71 in an undulating or serpentine fashion (e.g., a generally sinusoidal pattern, U-shaped, V-shaped, ovaloid-shaped, and the like) around a cylindrical mandrel. An open lumen in the interior of the wire-framed cylinder is created, and the ends of the wire-framed cylinder are open.

The cup frame 72 is formed so that it can be radially compressed to a low-profile configuration for placement in a delivery catheter or sheath (as will be described further below in reference to FIGS. 10A-10D).

The coil portion 74 of wire frame 70 generally includes the properties and features of wires 10, 10, 10, and 61 described above. In some embodiments, coil portion 74 is made from a wire 71 that is also used to form the cup frame 72.

Figure 8:
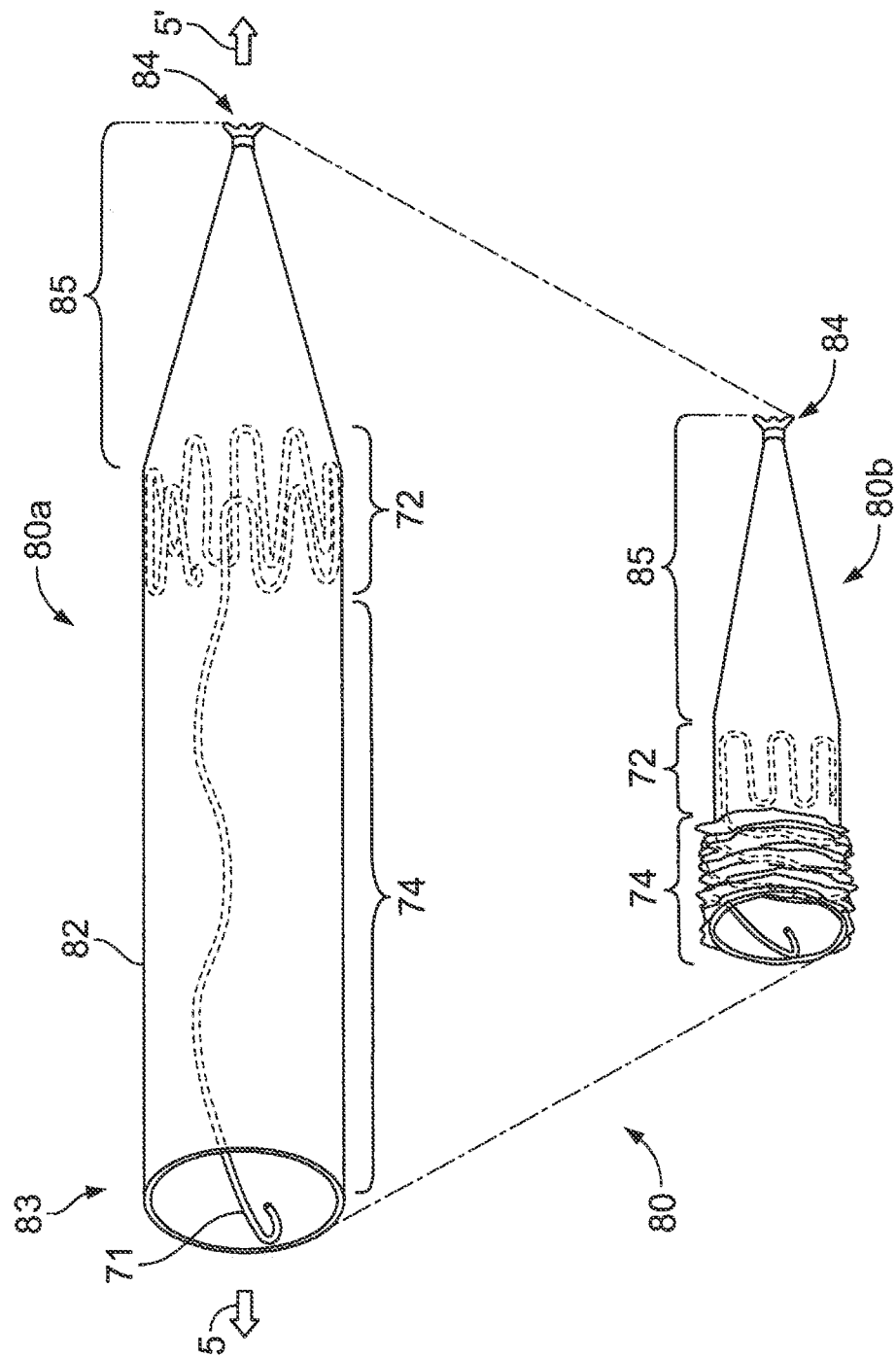
FIG. 8 depicts an example cup-shaped occlusion device in a stretched configuration and a relaxed configuration.
Figure 9:
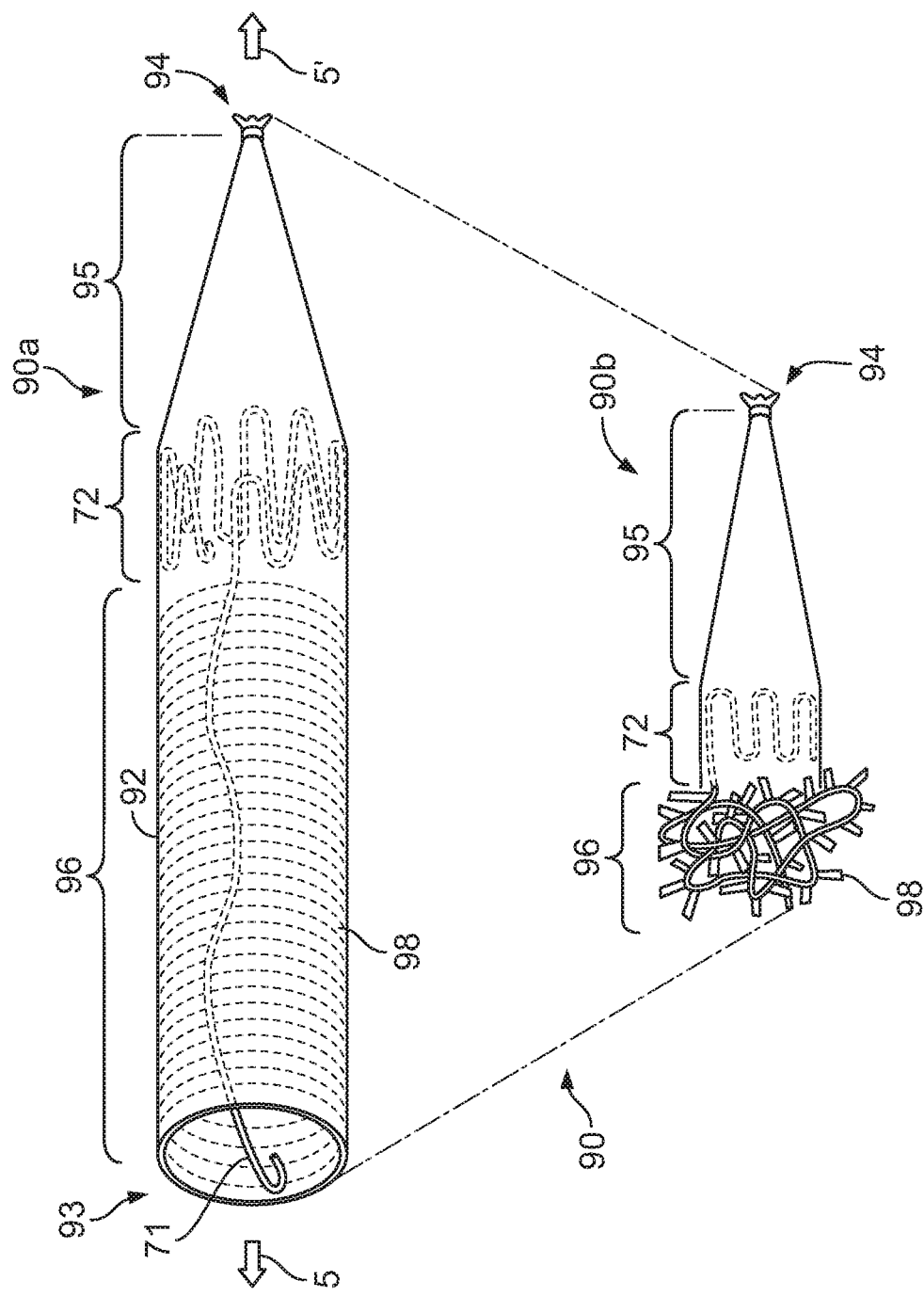
FIG. 9 depicts an example cup-shaped occlusion device in a stretched configuration and a relaxed configuration.

With reference to FIG. 8, an example cup-shaped occlusion device 80 includes a wire 71 and a membranous tube 82. The example cup-shaped occlusion device 80 is shown in a low-profile configuration 80a and a relaxed configuration 80b (again depending on presence or absence of stretch forces 5 and 5').

Wire 71 of example cup-shaped occlusion device 80 can be configured, for example, as the wire frame 70 described in reference to FIG. 7. That is, in some embodiments wire 71 can have a cup frame portion 72 and a coil portion 74. A membranous tube 82 can be affixed to wire 71, continuously or intermittently, using any of the variety of methods described above (e.g., adhesives, stitching, friction, weaving, interference, etc.).

The membranous tube 82 can be constructed using any of the materials, treatments, and manufacturing methods described above in regard to membranous materials. For example, in some embodiments, the membranous tube 82 is an extruded polymeric film tube. In some embodiments, the membranous tube 82 is a helically-wound strip of membranous material. In some embodiments, the membranous tube 82 has a woven or knitted construction.

Membranous tube 82 includes a distal end 83 and a proximal end 84. The proximal end 84 is a closed end of the membranous tube 82. In some embodiments, the distal end 83 is an open end of the membranous tube 82. In some embodiments, the distal end 83 is a closed end of the membranous tube 82.

A membranous cup portion 85 is located at the proximal end 84. In some embodiments, the membranous cup portion 85 can be formed by simply gathering and cinching the membranous tube 82 at the proximal end 84. A clip device, purse string sutures, or similar methods can be used to cinch closed the membranous tube 82 to create the cup portion 85. In some embodiments, the membranous cup portion 85 can be sewn or cohered to create a conical, semispherical, cylindrical, or other similar three-dimensional cup-like shape.

As will be described further in reference to FIG. 10D, when the example cup-shaped occlusion device 80 is implanted at a desired target site within a bodily lumen, cavity, vessel, or organ (for example, to treat endoleaks), the membranous cup portion 85 will be everted within the interior of cup frame 72. In that configuration, the cup portion 85 will be positioned to occlude or reduce the passage of fluids through the vessel or cavity.

With reference to FIG. 9, an example cup-shaped occlusion device 90 includes a wire 71 and a membranous tube 92. The membranous tube 92 includes a distal end 93 and a proximal end 94. The example cup-shaped occlusion device 90 is shown in a low-profile configuration 90a and a relaxed configuration 90b (again depending on presence or absence of stretch forces 5 and 5').

Example cup-shaped occlusion device 90 includes the properties and features of the example cup-shaped occlusion device 80 described above. In addition, example cup-shaped occlusion device 90 includes individual fringes 98.

In some embodiments the individual fringes 98 can be formed by making multiple transverse cuts to the membranous tube 92 in the distal portion 96. Fringe cut-lines are represented by the substantially radial lines shown in the low-profile configuration 90a. As with the embodiment described above in reference to FIG. 5, the individual cuts are not made fully around the circumference of the membranous tube 92. That is, an individual cut does not fully sever a portion of the membranous tube 92 so as to create multiple tubes. For example, in some embodiments the portions of the membranous tube 92 that are adjacent to the wire 71 are not cut. In some embodiments, the portions of the membranous tube 92 that (i) covers the wire cup frame and (ii) forms the membranous cup portion 95 are also not cut to create fringes.

When occlusion device 90 is allowed to assume its relaxed configuration 90a, the individual fringes 98 can project from the distal portion 96 so as to create a larger profile as compared to similar occlusion devices without fringes 98. The larger profile can be advantageous for certain implementations that are suited to having a higher occlusive and/or thrombogenicity properties.

FIGS. 10A-10D provide a series of illustrations to depict an example method of deploying an example cup-shaped occlusion device 90 within a vessel 110 using an example deployment system 100. The vessel 110 has a fluid (e.g., blood) flowing through it in a direction indicated by arrow 120, i.e., arrow 120 points in a distal direction. Therefore, the direction opposite of arrow 120 is the proximal direction. The example cup-shaped occlusion device 90 is the occlusion device described in reference to FIG. 9 above. However, other types of occlusion devices can be deployed using the methods provided here (or by using minor variations of the methods). The example delivery system 100 generally includes a delivery sheath (or catheter) 102 and a pusher catheter 104.

In FIG. 10A, the example deployment system 100 containing the example cup-shaped occlusion device 90 is depicted as approaching an implantation site within the vessel 110. The deployment system 100 includes a delivery catheter or sheath 102. In some embodiments, the delivery sheath 102 is a tube that is used to constrain an occlusion device in its low-profile delivery configuration, and to percutaneously deliver the occlusion device to a target deployment site within a bodily cavity or vessel. The tubular delivery sheath 102 can have a circular cross-section or another cross-sectional shape, such as ovular or other suitable shapes. A proximal end of the delivery sheath 102 can be attached to a deployment actuator (e.g., a handheld deployment actuator or a non-handheld deployment actuator) that can be operated by a clinician operator. In some embodiments, the deployment actuator provides one or more controls that permit a clinical operator to control one or more aspects of the delivery sheath 102. In some embodiments, the delivery sheath 102 is a steerable delivery sheath. In some embodiments, at least the distal end portion of the delivery sheath 102 is steerable. In some embodiments, a guidewire is installed in the patient first, and the delivery sheath 102 is installed over the guidewire. The delivery sheath 102 can have one lumen or multiple (e.g., two or more) lumens. In some embodiments, radiopaque markers are included on portions of the delivery sheath 102 (e.g., the tip) to assist with radiographic visualization of the delivery sheath 102 during the installation of the delivery sheath 102 into the body of a patient.

The delivery sheath 102 contains the example cup-shaped occlusion device 90. At this stage of the deployment process the cup-shaped occlusion device 90 is in a low-profile delivery configuration so as to fit within a lumen of the delivery sheath 102. To achieve the low-profile delivery configuration, the coil portion 74 is stretched axially to elongate the coil and to reduce its radial profile, and the cup frame 72 is radially compressed to reduce its radial profile. Once the occlusion device 90 resides within the delivery sheath 102, the delivery sheath 102 exerts containment forces on the occlusion device 90 to retain the occlusion device 90 in its low-profile delivery configuration.

The example deployment system 100 also includes a pusher catheter 104. In some embodiments, the pusher catheter 104 is a flexible polymeric tubular component. The pusher catheter 104 is located within a lumen of the delivery sheath 102. In some embodiments, the distal end of the pusher catheter 104 is releasably coupled to the occlusion device 90. In some embodiments, the proximal end of the pusher catheter 104 is coupled to a deployment actuator, and the deployment actuator provides one or more controls that permit a clinical operator to control one or more aspects of the pusher catheter 104. In other deployment system embodiments, other types of devices for constraining and remotely deploying an occlusion device (other than a pusher catheter) can be used.

In some embodiments, the pusher catheter 104 is releasably coupled to a connector element of the occlusion device 90. In some embodiments, the pusher catheter 104 is releasably coupled to the membranous sheet or wire portions of the occlusion device 90. In some embodiments, the pusher catheter 104 contains a looped suture, clip, clamp, or similar structure that releasably couples the pusher catheter 104 to the occlusion device 90. In some embodiments, the looped suture or similar structure is radiopaque.

In some embodiments, the pusher catheter 104 includes two or more lumens through which the looped suture 106 passes. That is, one portion of the looped suture 106 can pass through a first lumen in the pusher catheter 104 and a second portion of the looped suture 106 can pass through a second lumen in the pusher catheter 104. In some embodiments, the looped suture 106 can pass through a single lumen in the pusher catheter 104. In some embodiments, the looped suture 106 is a strand of suture material that is used to releasably couple the pusher catheter 104 to the occlusion device 90 by tethering them together. For example, the pusher catheter 90 of FIG. 10A illustrates a looped suture 106 attached to the membranous sheet of the occlusion device 90. In some embodiments, the looped suture 106 is a single length of suture material with both ends of the looped suture 106 located at the proximal end of the deployment system 100, such as at or near the deployment actuator coupled to the deployment system 100. In some embodiments, the looped suture 106 is routed from the proximal end of the deployment system 100, through a first lumen in the pusher catheter 104, exiting the first lumen at the distal end of the pusher catheter 104, coupling to the medical device, re-entering the distal end of the pusher catheter 104 via a second lumen, and running back through the second lumen to the proximal end of the deployment system 100. The clinician operator can tug on the ends of the looped suture 106 to snug the pusher catheter 104 to the occlusion device 90. When the pusher catheter 104 is snugged to the occlusion device 90, movement of the pusher catheter 104 will tend to induce a corresponding movement of the occlusion device 90. In some embodiments, one or both ends of the looped suture 106 are coupled to the deployment actuator, which may provide one or more controls permitting the clinical operator to control one or more aspects of the occlusion device 90.

In FIG. 10B, the delivery sheath 102 has been partially pulled back (translated proximally) while the pusher catheter 104 has been maintained substantially stationary. This relative movement between the delivery sheath 102 and the pusher catheter 104 has caused the distal portion 96 of the occlusion device 90 to emerge from the lumen of the delivery sheath 102. With the containment forces of the delivery sheath 102 on the distal portion 96 substantially removed, the distal portion 96 is freed to self-expand to seek its relaxed configuration. In turn, the distal portion 96 can contract axially and expand radially as the wire in the distal portion 96 seeks its natural relaxed coiled shape. In its relaxed state, distal portion 96 is radially expanded to entirely or partially fill the lumen of vessel 110.

In some deployment method implementations, the pusher catheter 104 can be pushed distally while the delivery sheath 102 is maintained substantially stationary. That relative movement between the delivery sheath 102 and the pusher catheter 104 can cause the distal portion 96 of the occlusion device 90 to emerge from the lumen of the delivery sheath 102, similarly to the method of pulling back the delivery sheath 102 described above. In some deployment method implementations, a combination of the two methods are used.

Figure 10C:
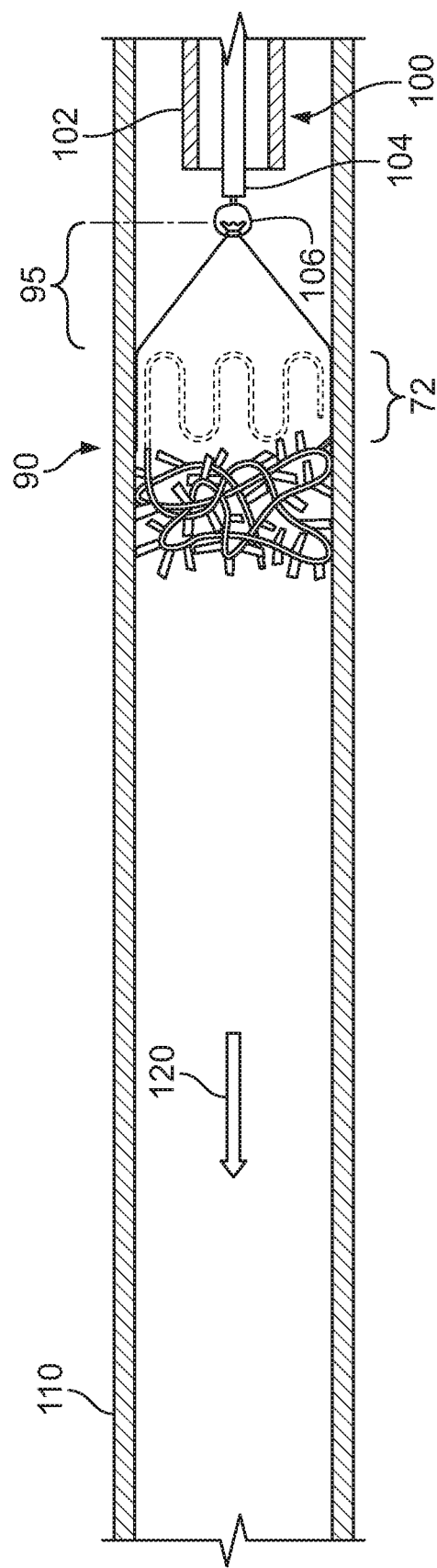

In FIG. 10C, the delivery sheath 102 has been further pulled back proximally while the pusher catheter 104 has been maintained substantially stationary. This relative movement between the delivery sheath 102 and the pusher catheter 104 has caused the entire occlusion device 90 to emerge from the lumen of the delivery sheath 102. With the containment forces of the delivery sheath 102 on the occlusion device 90 removed, the cup frame 72 is freed to self-expand to seek its relaxed configuration. In turn, the cup frame 72 can expand radially as the wire in the cup frame 72 seeks its natural relaxed shape. In its relaxed state, the cup frame 72 can radially expand to fully or partially become adjacent to the inner walls of vessel 110. The membranous cup portion 95 of the occlusion device 90 is also emerged from the delivery sheath 102 at this stage.

At this stage of the deployment process, the clinician operator can confirm the desirability of the position of the occlusion device 90 in relation to the surrounding bodily tissue. In some cases, clinicians use magnetic resonance imaging (MRI) or x-ray fluoroscopy imaging to visualize the positioning of the occlusion device 90. In general, the clinician may be interested in one or more of the position, location, orientation, anchoring strength, and the sealing properties of the occlusion device 90 in relation to the surrounding tissue. In some embodiments, radiopaque markers or jackets can be included on the occlusion device 90, such as on the wire and/or on the membranous material. In some embodiments that include a radiopaque looped suture 106, the adequacy of the fixation of the occlusion device 90 can be confirmed by inducing slack in the looped suture 106 and using radiography to visualize that the slack is maintained over a period of time.

In some implementations, to simulate the likely position that the occlusion device 90 may take after being released from the looped suture 106, the clinician operator may loosen, but not fully release, the looped suture 106 from its hold on the occlusion device 90. That is, the clinician may induce some slack in the looped suture 106 so that it is not tightly engaged with the occlusion device 90. Loosening the looped suture 106 may mitigate some of the positional influence that the looped suture 106 may be exerting on the occlusion device 90 as a result of their engagement. With the looped suture 106 loosened, the clinician can assess the positioning and anchorage strength of the occlusion device 90 with respect to the surrounding tissue. If the clinician is not satisfied with the positioning or anchorage strength of the occlusion device 90, the looped suture 106 can be retightened in order to restore the ability to reposition the occlusion device 90 by manipulating the pusher catheter 104 and looped suture 106.

The clinician operator may manipulate the occlusion device 90 using the pusher catheter 104 for various purposes. The manipulation of the pusher catheter 104 can serve to reposition and/or seat the occlusion device 90 to the tissue at the deployment site. In some embodiments, anchoring devices (e.g., barbs, protrusions, etc.) are included on the occlusion device 90. In those embodiments, manipulation of the pusher catheter 104 can help to embed the anchoring devices into or onto the surrounding tissue.

If the clinician is dissatisfied with the position or anchorage strength of the occlusion device 90, the clinician can retrieve and re-contain the occlusion device 90 within a lumen of the delivery sheath 102. To do so, the clinician can, for example, advance the delivery sheath 102 distally, while substantially maintaining the axial position of the pusher catheter 104 which is affixed to the occlusion device 90 by the looped suture 106. After re-capturing the occlusion device 90 within the delivery sheath 102, the clinician operator can repeat the process steps described above for deploying the occlusion device 90. In some embodiments, a common snare can also be used to assist in the recapture the occlusion device 90.

When the clinician operator is satisfied with the positioning of the occlusion device 90, the clinician can release the occlusion device 90 from the deployment system 100. For example, the clinician can remove the looped suture 106 from engagement with the occlusion device 90. To disengage the looped suture 106 from the occlusion device 90, the clinician operator can release one end of the looped suture 106 and pull on the other end of the looped suture 106 to draw a suitable length of the looped suture 106 out from the pusher catheter 104. After drawing the suitable length of the looped suture 106 from the pusher catheter 104, the looped suture 106 will become disengaged from the occlusion device 90. At this stage, the occlusion device 90 has been fully decoupled from the deployment system 100. In some embodiments, the looped suture 106, or other device used to couple the pusher catheter 104 to the occlusion device 90, may be detached from the pusher catheter 104 at the time of deployment and allowed to flow with the fluid into the everted membranous cup portion 95 for packing purposes.

Figure 10D:
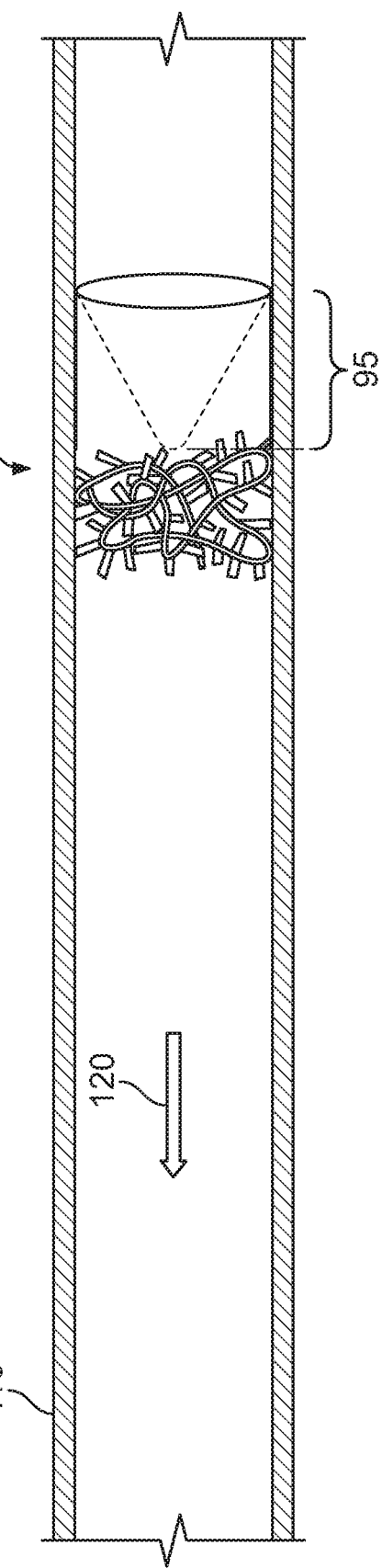

In FIG. 10D, the occlusion device 90 is shown in its deployed configuration within vessel 110. The delivery system 100 has been withdrawn from the implantation site. The membranous cup portion 95 has transitioned to an everted cup orientation. That is, the membranous cup portion 95 has moved distally to within the lumen defined by the cup frame 72 (cup frame 72 is not shown in this view so that the everted membranous cup portion 95 can be more clearly visualized). In this orientation, the membranous cup portion 95 is well positioned to occlude the fluid that would tend to flow through vessel 110.

The transition of the membranous cup portion 95 to the everted cup orientation can take place in various manners. In some implementations, the membranous cup portion 95 will become everted as a result of the fluid pressures within the vessel 110. For example, since the flow in vessel 110 is in the direction of arrow 120, the membranous cup portion 95 may naturally become everted by the pressure exerted by the fluid. This can be analogized to the functioning of a windsock. As axial fluid flow continues into everted cup, it produces radial pressure sufficient to expand the cup to its fluid capacity. In some implementations, the membranous cup portion 95 will become everted as a result of an action of the clinician operator. For example, the clinician may use the pusher catheter 104 to nudge the membranous cup portion 95 to the everted orientation. In some implementations, a combination of such factors may cause the membranous cup portion 95 to become everted to within the cup frame 72.

The everted membranous cup portion 95 may have various volumetric capacities. In some embodiments, the everted membranous cup portion 95 has a capacity that does not fill the entire internal space defined by the cup frame 72. In some embodiments, the everted membranous cup portion 95 may have a fluid capacity equivalent to or greater than the volume within the internal space formed by the cup frame 72. In some such embodiments, the everted membranous cup portion 95 is designed to prevent the addition of substantial radial forces from the membranous cup portion 95 onto the cup frame 72. In some such embodiments, the filling of the everted membranous cup portion 95 with fluid and the resulting radial expansion of the everted membranous cup portion 95 will press it against the internal surface of the cup frame 72, and in some embodiments also against the walls of the vessel lumen, thereby aiding in preventing migration of the device. In some embodiments, the membranous cup portion 95 is designed to create only a limited amount of radial force so that the potential for rupture of the bodily lumen, cavity, vessel, or organ is mitigated.

As described above, some embodiments of cup-shaped occluder devices include a cup frame 72 portion, but no coil portion is included. In some embodiments, the occluder device embodiment includes a membranous cup portion but may not include an additional membranous occluder portion (i.e., portion 74 of FIG. 8 and portion 96 of FIG. 9 may not be included). In some such embodiments, it is evident that a longer everted membranous cup portion 95 whose distal end (when everted) extends past the distal end of the cup frame 72 may increase the surface contact of the everted membranous cup portion 95 with the vessel wall, thereby increasing the migration resistance of the occlusion device. As such, the membranous cup portion 95 may be sized such that it extends 5, 10, 15, 20, 25, 30, 35, 40 mm or more past the distal end of the cup frame 72. In addition, the membranous cup portion 95 may be volumetrically sized so, when fully expanded, its diameter is slightly larger than the inner diameter of the cup frame 72. As such, the membranous cup portion 95 will be able to bulge through the spaces between winds of the cup frame 72 to contact the wall surface of the vessel along all or at least a portion of the length of the occlusion device.

The wire of occlusion device 90 may include one or more fixation elements (e.g., anchors, barbs, protrusions, and/or penetrating members) which engage the cup frame 72 with the wall of the vessel 110 to prevent migration of the occlusion device 90 after deployment within the vessel 110. Likewise, in embodiments wherein the surface of the everted membranous cup portion 95 contacts the wall of the vessel, the membranous sheet material may include features to increase friction between the cup surface and wall of the lumen. For example, in some embodiments a coating that imparts a rough surface texture can be applied to the membranous sheet. Coatings, including granules of polymeric materials, are known in the art and may be used to impart a textured surface to the membranous sheet material to impart increased frictional properties to prevent movement of the occlusion devices provided herein. For example, the polymers heat-treated with polyfluorocarbon granules as described in co-owned and pending U.S. Publication No. 2012/0064273 entitled "Porous Article", filed Sep. 10, 2010 and hereby incorporated by reference in its entirety, are suitable for use with the membranous cup portion 95.

As discussed above, to facilitate in vivo placement of the occlusion devices, a radiopaque material may be incorporated to allow for detection of the position of the device within a bodily lumen, cavity, vessel, or organ. A number of radiopaque materials and coatings are well known in the art which may be incorporated onto the surface of the device or otherwise integrated into the device. By way of illustration, such materials include gold, platinum, platinum-tungsten, palladium, platinum-iridium, rhodium, tantalum, or alloys or composites thereof. The radiopaque materials may be incorporated over the entire device or in discrete regions, and in any number of patterns, to allow for radiographic detection. For example, in some embodiments at least the distal end of the wire includes radiopaque materials.

Upon deployment into a bodily lumen, cavity, vessel, or organ the occlusion devices provided herein obstruct fluid flow to occlude the bodily lumen, cavity, vessel, or organ. In some embodiments, the occlusion devices also promote one or more of thrombus formation and endothelialization.

Figure 11:
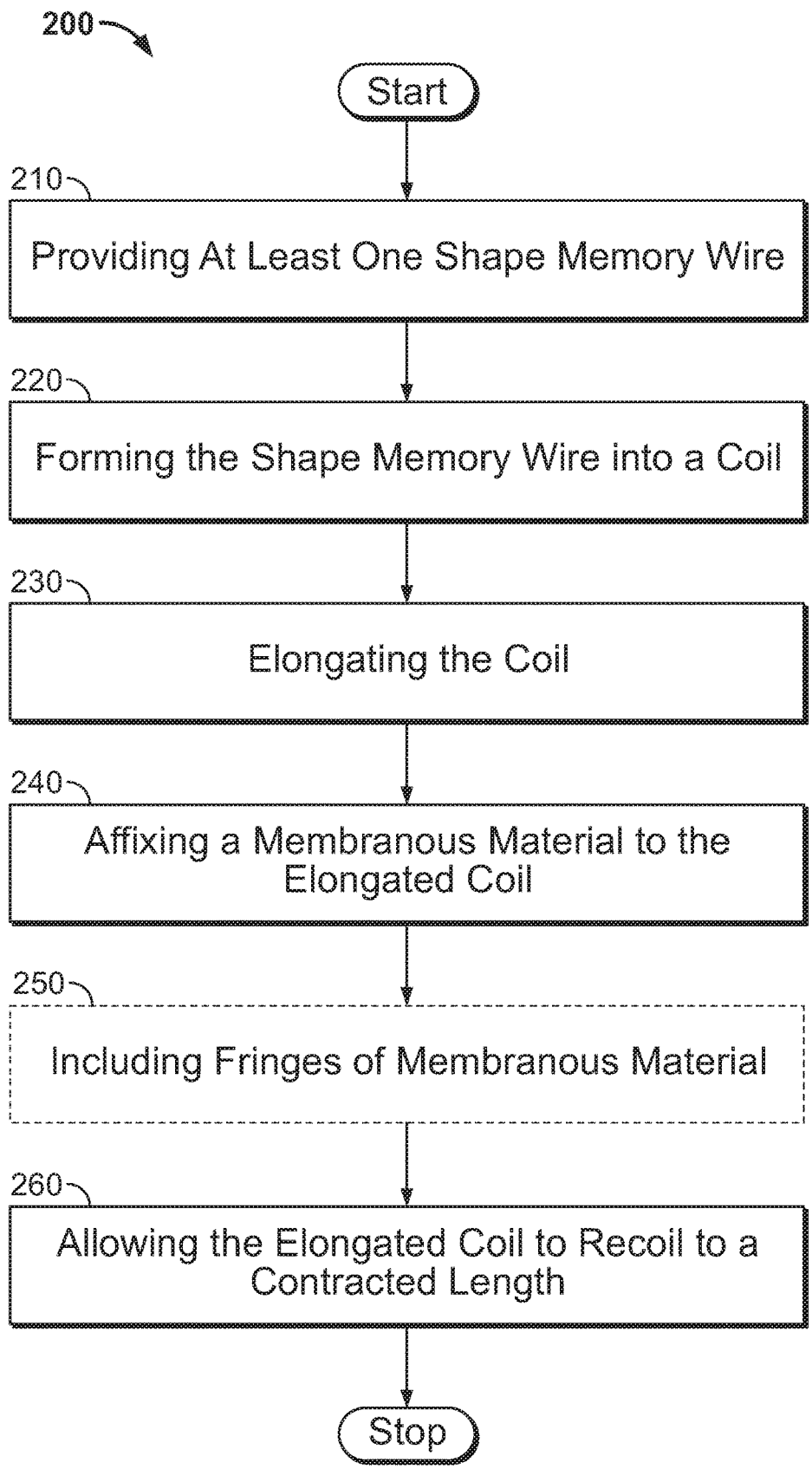
FIG. 11 is a flowchart of an example process for making a coil occlusion device.

FIG. 11 depicts an example process 200 for manufacturing occlusion devices such as the coil occlusion devices described above in reference to FIGS. 1-6F. The materials and manufacturing methods described above in reference to the occlusion devices are applicable to process 200. The description of process 200 includes concise statements regarding its operational steps which can assist the reader to correlate the steps of process 200 to relevant subject matter from above.

The process 200 begins at operation 210 where at least one shape memory wire is provided. As described above, the wire can comprise any suitable biocompatible material, such as metallic or polymeric materials. In some embodiments, the wire is a super-elastic alloy material.

At operation 220, the wire can be formed into a coil shape. In some embodiments, the wire is wound onto a mandrel to form the coil shape. In some embodiments, the wire that is wound into a coil shape is heat-set so that the wire memorizes the coiled shape. In some embodiments, the wire is plastically deformed into the coil shape. A variety of coil shapes can be used. FIGS. 6A-6F provide some illustrative examples.

At operation 230 the coil is elongated. In some embodiments, the coil is elongated by stretching the coil. That is, the coil can be elongated by pulling apart or displacing the ends of the coil in opposite directions. In some embodiments, the elongated coil is substantially linear. In some embodiments, the elongated coil has an undulating shape that is reminiscent of the coiled shape of the wire. The elongated coil has a length that is greater than the coil prior to elongation. The elongated coil has a diameter that is less than the overall diameter of the coil prior to elongation.

At operation 240, a membranous material is affixed to the elongated coil. In some embodiments, the membranous material is a strip of material. In some embodiments, the membranous material is a strip that is wound onto or folded over the elongated coil. In some embodiments, the membranous material is a tube that surrounds the elongated coil. In some embodiments, the tube is made by winding a membranous strip. In some embodiments, the tube is knitted, woven, or extruded. In some embodiments, the membranous material is affixed to the elongated coil by an adhesive, by friction, by an interference fit, or by weaving the elongated coil within the membranous material, to name some examples. In some embodiments, the membranous material is affixed to the elongated coil so as to provide a fringe portion, i.e., a portion of membranous material that is not in direct contact with the elongated coil.

At operation 250, optionally, fringes of membranous material can be formed or added on the occlusion device. In some embodiments, the fringes are formed by incising the membranous material. In some embodiments, the fringes are an additional portion of membranous material that is affixed to the occlusion device.

At operation 260, the elongated coil with the affixed membranous material can be allowed to recoil to a contracted coil shape. In some embodiments, the elongated coil will be biased to contract to a coiled shape as a result of operation 220. In some embodiments, this operation will cause the membranous material that is affixed to the elongated coil to also become be rearranged, i.e., the membranous material will become bunched up or compressed into a wad.

Figure 12:
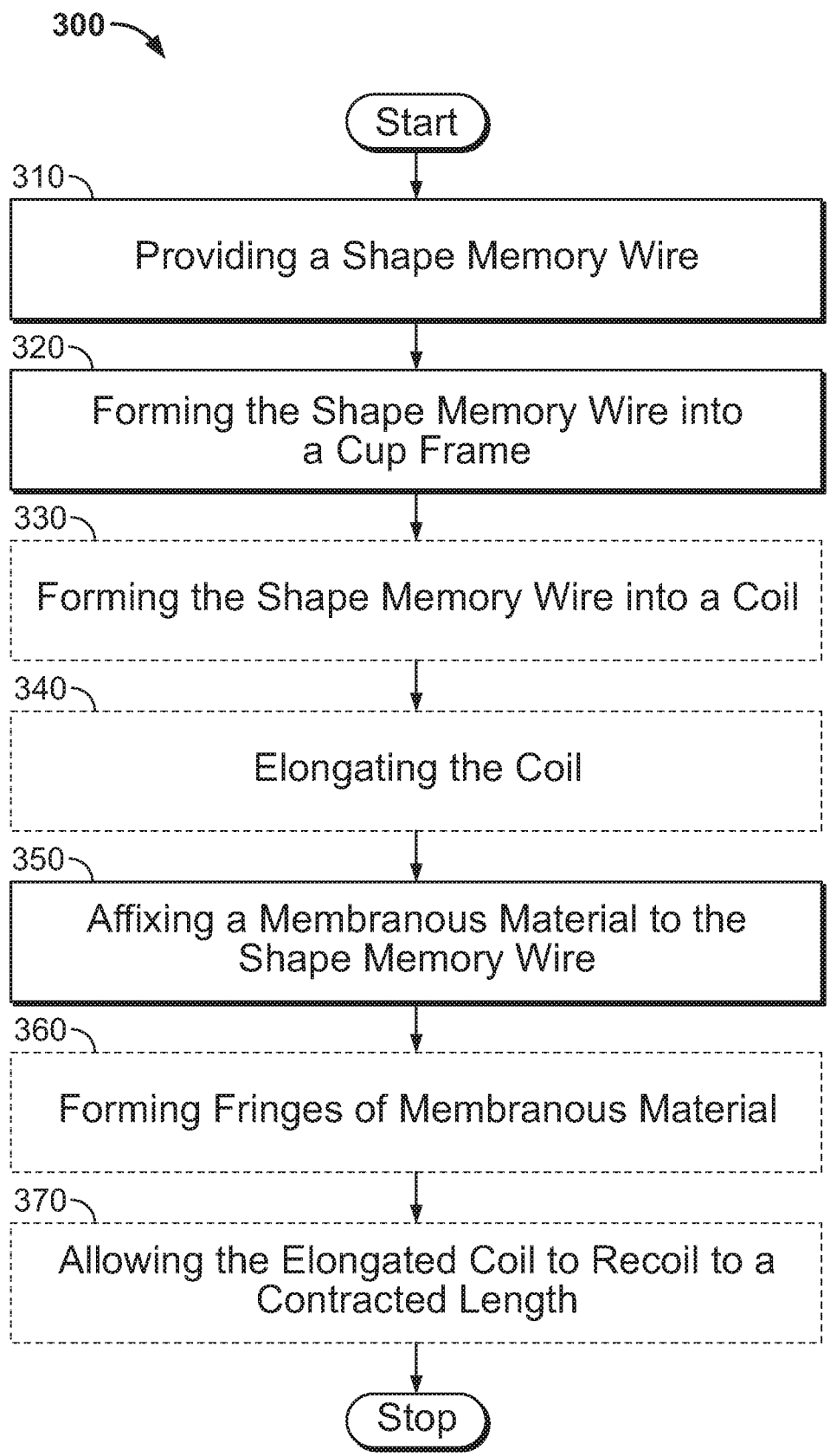
FIG. 12 is a flowchart of an example process for making a cup-frame occlusion device.

FIG. 12 depicts an example process 300 for manufacturing occlusion devices such as the cup-shaped occlusion devices described above in reference to FIGS. 8 and 9. The materials and manufacturing methods described above in reference to the occlusion devices are applicable to process 300. The description of process 300 includes concise statements regarding its operational steps which can assist the reader to correlate the steps of process 300 to relevant subject matter from above.

The process 300 begins at operation 310 where one or more shape memory wires are provided. As described above, the wire can comprise any suitable biocompatible material such as metallic or polymeric materials. In some embodiments, the wire is a super-elastic alloy material.

At operation 320, the one or more wires are formed into a cup frame. In some embodiments, the cup frame is a wire-framed open cylinder. In some embodiments, the cup frame can be formed by bending the wire in an undulating or serpentine fashion (e.g., a generally sinusoidal pattern, U-shaped, V-shaped, ovaloid-shaped, and the like) around a cylindrical mandrel. In some embodiments, an open lumen in the interior of the wire-framed cylinder is created, and the ends of the wire-framed cylinder are open. In some embodiments, the cup frame is formed so that it can be radially compressed to a low-profile configuration for placement in a delivery catheter or sheath.

At operation 330, the one or more wires can be optionally formed into a coil. As described above with reference to FIG. 7, in some embodiments the wire used to form the coil is the same wire(s) that the cup frame is made of. In some embodiments, the wire used to form the coil is a wire that is separate from the wire(s) that the cup frame is made of. Various types of coils can be formed (see, e.g., FIGS. 6A-6F).

At operation 340, if the occlusion device being made includes the optional coil, the one or more wires used to form the coil can be elongated. In some cases, the coil is elongated by stretching the coil. That is, the coil can be elongated by pulling apart or displacing the ends of the coil in opposite directions. In some embodiments, the elongated coil is substantially linear. In some embodiments, the elongated coil has an undulating shape that is reminiscent of the coiled shape of the wire. The elongated coil has a length that it greater than the coil prior to elongation. The elongated coil has a diameter that is less than the overall diameter of the coil prior to elongation.

At operation 350, a membranous material is affixed to the shape memory wire. In some embodiments, the membranous material is a tube that surrounds the cup frame and the optional elongated coil. In some embodiments, the tube is an extruded film material. In some embodiments, the tube is made by winding a membranous strip. In some embodiments, the tube is knitted or woven. In some embodiments, the membranous material is a strip of material. In some embodiments, the membranous material is a strip that is wound onto or folded over the cup frame and optional elongated coil. In some embodiments, the membranous material is affixed to the wire by an adhesive, by friction, by an interference fit, or by weaving the elongated coil within the membranous material—to name some examples.

The membranous material is applied to the wire such that a cup-shaped portion of membranous material is affixed to the cup frame. In some embodiments, the membranous cup-shaped portion is located at and affixed to the proximal end of the cup frame. In some embodiments, the membranous cup-shaped portion is formed by simply gathering and cinching the membranous tube at the proximal end (see, e.g., FIG. 8). A clip device, purse string sutures, or similar methods can be used to cinch closed the membranous tube to create the cup-shaped portion. In some embodiments, the membranous cup-shaped portion can be sewn or cohered to create a conical, semispherical, cylindrical, or other similar three-dimensional cup-like shape.

At operation 360, optionally, fringes of membranous material can be formed on the occlusion device. In some embodiments, the fringes can be optionally formed of (or added onto) the membranous material affixed to the optional elongated coil. In some embodiments, the fringes are formed by incising the membranous material. In some embodiments, the fringes are an additional portion of membranous material that is affixed to the occlusion device.

At operation 370, the optional elongated coil with the affixed membranous material can be allowed to recoil to a contracted coil shape. In some embodiments, the elongated coil will be biased to contract to a coiled shape as a result of operation 330. In some embodiments, this operation will cause the membranous material that is affixed to the elongated coil to also become be rearranged, i.e., the membranous material will become bunched up or compressed into a wad.

Figure 13:
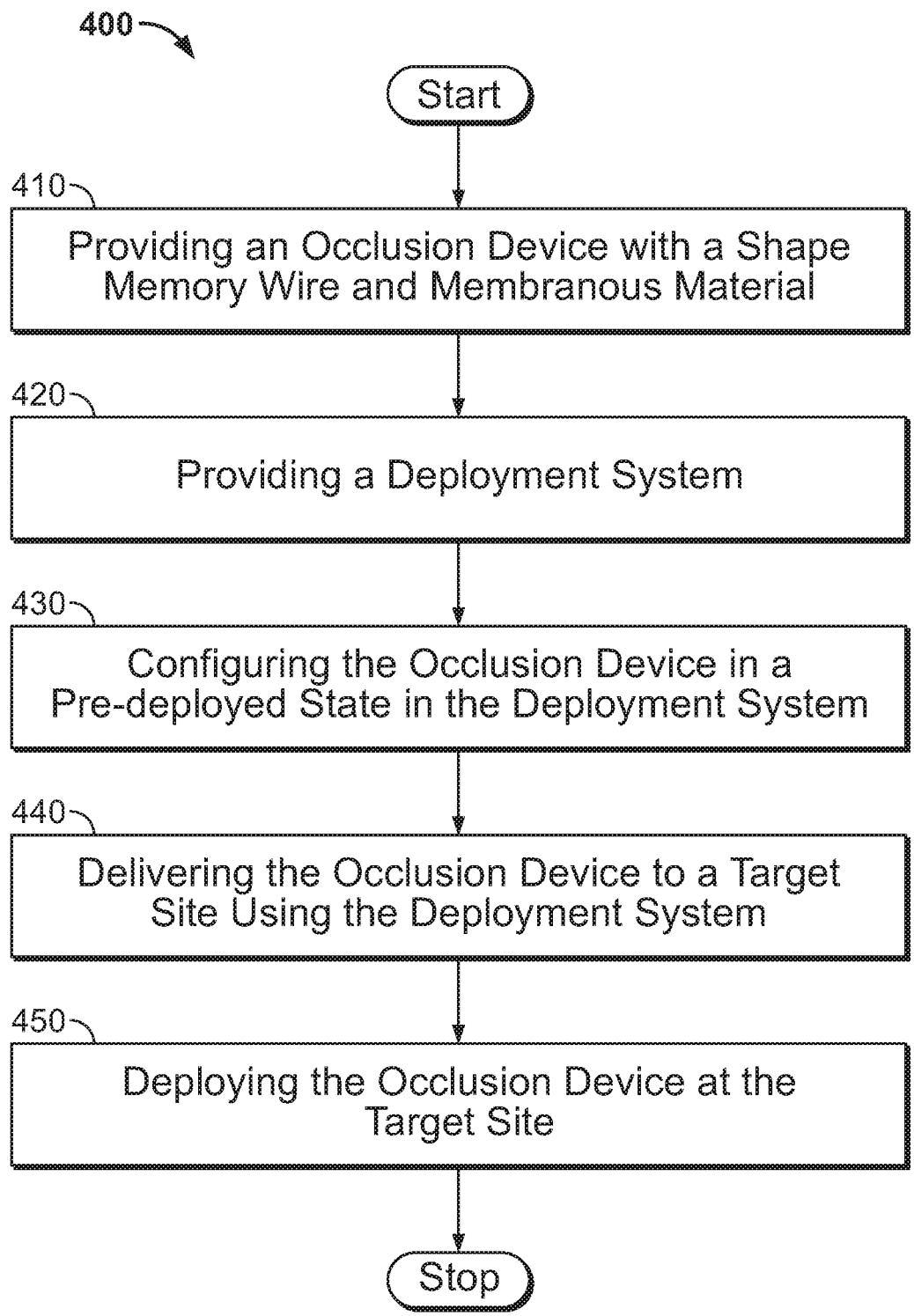
FIG. 13 is a flowchart of an example method of implanting an occlusion device in the body of a patient.

FIG. 13 depicts an example method 400 for implanting an occlusion device at a target site within a bodily lumen, cavity, vessel, or organ. The method 400 is a transcatheter or percutaneous method for implanting an occlusion device.

The method 400 starts at operation 410 where an occlusion device with a shape memory material wire and membranous material is provided. For instance, the occlusion device can be any of the embodiments of occlusion devices described herein.

At operation 420, a deployment system is provided. In some embodiments of method 400, the deployment system is like the deployment system 100 described in reference to FIGS. 10A-10D. In some embodiments of method 400, other types of deployment systems for percutaneous device delivery are utilized.

At operation 430, the occlusion device is configured in a pre-deployed state in the deployment system. In some occlusion device embodiments, the pre-deployed state is a low-profile state achieved by deflecting the shape memory wire of the device. For example, occlusion devices with a coil can be configured in a pre-deployed low-profile state by stretching the coil (i.e., displacing and maintaining the positions of the ends of the coil in opposite directions). Occlusion device embodiments having a cup frame can be configured in a pre-deployed low-profile state by radially compressing the cup frame portion. An occlusion device that is configured in a pre-deployed low-profile state can be placed within a component of the deployment system. For example, in some embodiments, the occlusion device can be placed within a lumen of a delivery catheter or sheath.

At operation 440, the occlusion device is delivered to a target site using the deployment system. The target site may be a particular location in a bodily lumen, cavity, vessel, or organ. In some embodiments, the delivery system is used to traverse the vasculature of a patient to a target site. In some embodiments, the delivery system is steerable using a controller device that is operable by a clinician. In some embodiments, a system for visualizing the position of the deployment system and/or occlusion device is used (e.g., an x-ray fluoroscopy system).

At operation 450, the occlusion device is deployed at the target site within the bodily lumen, cavity, vessel, or organ. In some embodiments, a pusher catheter is used to eject the occlusion device from a lumen of a delivery catheter. In some embodiments, the occlusion device reconfigures its size and shape as a result of the deployment from the delivery catheter. In some embodiments, the reconfigured occlusion device is positioned within the bodily lumen, cavity, vessel, or organ so as to reduce or eliminate fluid flow in the area of the occlusion device.

Some embodiments of the occlusion devices provided herein, and methods of their manufacture and use, are further illustrated by the examples below.

EXAMPLE 1

Manufacture of a Fringed Occlusion Device

A fringed occlusion device for blocking fluid flow through a lumen in a bodily tissue was produced as follows.

A NiTi wire was heat-treated to memorize and assume a helical coil shape when deployed. The wire was extended by stretching it to a linear configuration. A polyfluorocarbon (ePTFE) sheet was wrapped in two layers around the wire and thermally bonded (in a 320° C. oven for three minutes) to the wire.

A loose, unsecured edge of the polymer sheet was left open along the length of the wire. Random cuts were made into the loose edge to form an external fringe along the length of the device.

EXAMPLE 2

Manufacture of a Fringed Occlusion Device

A fringed occlusion device for blocking blood flow through a lumen in a bodily tissue was produced as follows.

A NiTi wire was heat-treated to memorize and assume a helical coil shape when deployed. The wire was extended by stretching to a linear configuration. A polyfluorocarbon (ePTFE) sheet was wrapped in a layer around the wire and thermally treated by thermally bonding (in a 320° C. oven for three minutes) to the wire. Random cuts were made into the tube to form an external fringe along the length of the device.

The wire was allowed to assume a partially pre-deployed shape (loose coil). The cuts were sufficient in number and location to relieve the tension exerted on the tube by the coil so it could be stretched for loading into a delivery catheter.

EXAMPLE 3

Occlusion Using a Fringed Occlusion Device

Occlusion of a lumen (vascular lumen model) by a fringed occlusion device manufactured as described in Example 2 was tested under the conditions noted below.

Testing Pressure (target 125 mm Hg): 125 mm Hg
Delivery Catheter ID: 6 french
Pressure Post Deployment: 72 mm Hg Substantially complete occlusion of the lumen without migration of the device at post-deployment pressures of 1.4 psi was demonstrated. The device was successfully retrieved intact from the lumen following testing.

EXAMPLE 4

Manufacture of an Occlusion Device with a Fluid Capture Cup

An occlusion device with a fluid capture cup was produced as follows:

A nitinol wire was heat-treated to memorize and assume a helical coil shape when deployed. While it its deployed, helical coil state, the open end of a polyfluorocarbon cup was secured by thermally bonding to at least one full turn of the coiled wire.

EXAMPLE 5

Manufacture of an Occlusion Device with a Fluid Capture Cup

An occlusion device with a fluid capture cup was produced as follows:

A nitinol wire was heat-treated to memorize and assume a helical coil shape when deployed. With the wire in it its longitudinally extended state, a sheet of ePTFE coated with FEP granules with a conical closed end was wrapped around the wire and heat-secured to it (in a 320° C. oven for three minutes). The tip of the conical closed end was a solid plug that was pierced to form a through bore for insertion of a looped suture.

EXAMPLE 6

Fluid Flow Into an Occlusion Device with a Fluid Capture Cup

Capture of axial fluid flow through the center of the coil of the device described in Example 5 was tested in a model of fluid dynamics.

At 125 mm Hg, fluid flow through an 8 mm luminal space (tube) caused complete eversion of the cup into the center of the coil. Blood captured within the everted cup caused it to radially expand, pressing the outer surface of the cup against the inner surface of the coil.

While this specification contains many specific implementation details, these should not be construed as limitations on the scope of any devices, methods, and systems discussed herein, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of making an implantable occlusion device, comprising:
   providing at least one shape memory wire;
   forming the shape memory wire into a coil, the coil having an overall outside diameter and a coil length;
   providing a flexible polymeric tube, the flexible polymeric tube having an inside diameter that is smaller than the overall outside diameter of the coil;
   elongating the coil, wherein the elongated coil has an elongated coil length that is greater than the coil length, and wherein the elongated coil has an elongated coil diameter that is less than the overall outside diameter of the coil;
   fitting the flexible polymeric tube over an outer circumference the elongated coil; and
   allowing the elongated coil to recoil to a contracted length, wherein the contracted length is less than the elongated coil length, thereby causing the flexible polymeric tube to form an irregular shape useful for occlusion and the coil taking non-linear forms other than a helix within the flexible polymeric tube.

2. The method of claim 1, wherein the flexible polymeric tube comprises ePTFE.

3. The method of claim 1, further comprising attaching the flexible polymeric tube to the elongated coil prior to allowing the elongated coil to recoil to the contracted length.

4. The method of claim 3, wherein the flexible polymeric tube is attached to the elongated coil on an entire length of the wire.

5. The method of claim 3, wherein the flexible polymeric tube is attached to the elongated coil at multiple discrete attachment points along a length of the wire.

6. The method of claim 3, wherein the flexible polymeric tube is attached to the elongated coil by an interference fit between the inside diameter of the flexible polymeric tube and the overall outside diameter of the coil.

7. The method of claim 3, wherein the flexible polymeric tube is attached to the elongated coil by an adhesive.

8. The method of claim 1, further comprising, prior to allowing the elongated coil to recoil to the contracted length, incising the flexible polymeric tube to create a fringe portion along at least a portion of a length of the flexible polymeric tube.

9. A method of making an implantable occlusion device, comprising:
   providing at least one shape memory wire;
   forming the shape memory wire into a coil, the coil having an overall outside diameter;
   elongating the coil, thereby increasing a length of the coil to an elongated length and reducing the overall outside diameter of the coil;
   wrapping a flexible polymeric material onto the elongated coil, wherein the elongated coil is substantially covered by the flexible polymeric material, and wherein portions of the flexible polymeric material are not in direct contact with the elongated coil; and
   allowing the elongated coil to recoil to a contracted length, wherein the contracted length is less than the elongated length, thereby causing the flexible polymeric material to form a pleated shape useful for occlusion, and the elongated coil taking non-linear forms other than a helix within the flexible polymeric tube.

10. The method of claim 9, wherein the flexible polymeric material comprises ePTFE.

11. The method of claim 9, further comprising attaching the flexible polymeric tube to the elongated coil prior to allowing the elongated coil to recoil to the contracted length.

12. The method of claim 9, further comprising attaching the flexible polymeric material to the elongated coil on an entire length of the wire.

13. The method of claim 9, further comprising attaching the flexible polymeric material to the elongated coil at multiple discrete attachment points along a length of the elongated coil.

14. The method of claim 9, further comprising attaching the flexible polymeric material to the elongated coil using an adhesive.

15. The method of claim 9, further comprising, prior to allowing the elongated coil to recoil to the contracted length, incising the flexible polymeric material to create a fringe portion along at least a portion of a length of the flexible polymeric material.

16. A method of making an implantable occlusion device, comprising:
   providing at least one shape memory wire;
   forming the shape memory wire into a cup frame, the cup frame having an overall outside diameter and open proximal and distal ends;
   affixing a flexible polymeric cup to the proximal end of the cup frame, wherein the flexible polymeric cup includes an open end and a closed end, wherein the open end is affixed to the cup frame, wherein the flexible polymeric cup is adapted to be reconfigured during implantation in a bodily lumen from a pre-deployed state to an everted state, and wherein the flexible polymeric cup in the everted state is adapted to occlude the lumens
   forming the shape memory wire into a coil; and
   fitting a flexible polymeric tube over the elongated coil, wherein the coil has an overall outside diameter, the coil taking non-linear forms other than a helix when allowed to recoil.

17. The method of claim 16, further comprising:
elongating the coil, wherein the elongated coil has an elongated coil length that is greater than the coil length, and wherein the elongated coil has an elongated coil diameter that is less than the overall outside diameter of the coil; and
allowing the elongated coil to recoil to a contracted length, wherein the contracted length is less than the elongated coil length, thereby causing the flexible polymeric tube to form an irregular shape useful for occlusion.

18. The method of claim 17, further comprising, prior to allowing the elongated coil to recoil, incising the flexible polymeric tube to create a fringe portion along at least a portion of a length of the flexible polymeric tube.

19. The method of claim 16, further comprising:
elongating the coil, thereby increasing a length of the coil to an elongated length and reducing the overall outside diameter of the coil;
wherein the elongated coil is substantially covered by the flexible polymeric material, and wherein portions of the flexible polymeric material are not in direct contact with the elongated coil; and
allowing the elongated coil to recoil to a contracted length, wherein the contracted length is less than the elongated length, thereby causing the flexible polymeric material to form an irregular shape useful for occlusion.

20. The method of claim 19, further comprising, prior to allowing the elongated coil to recoil, incising the flexible polymeric material to create a fringe portion along at least a portion of a length of the flexible polymeric material.

* * * * *